US010555825B2

(12) United States Patent
Gong et al.

(10) Patent No.: US 10,555,825 B2
(45) Date of Patent: Feb. 11, 2020

(54) ROTATION OF A MEDICAL DEVICE DURING CRIMPING

(71) Applicant: Abbott Cardiovascular Systems Inc., Santa Clara, CA (US)

(72) Inventors: Victoria M. Gong, Sunnyvale, CA (US); Stephen Pacetti, San Jose, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 99 days.

(21) Appl. No.: 15/807,963

(22) Filed: Nov. 9, 2017

(65) Prior Publication Data

US 2019/0133798 A1    May 9, 2019

(51) Int. Cl.
| | | |
|---|---|---|
| *A61F 2/958* | (2013.01) |
| *B23P 19/02* | (2006.01) |
| *B23P 11/02* | (2006.01) |
| *A61F 2/95* | (2013.01) |
| *B25B 27/14* | (2006.01) |
| *A61F 2/82* | (2013.01) |
| *B21D 39/04* | (2006.01) |

(52) U.S. Cl.
CPC ............ *A61F 2/958* (2013.01); *B23P 11/025* (2013.01); *B23P 19/02* (2013.01); *B25B 27/146* (2013.01); *A61F 2/82* (2013.01); *A61F 2002/9522* (2013.01); *A61F 2002/9583* (2013.01); *A61F 2240/001* (2013.01); *B21D 39/046* (2013.01)

(58) Field of Classification Search
CPC .............. A61F 2/958; A61F 2002/9522; A61F 2002/9583; A61F 2240/001; H01R 43/04; H01R 43/048; B23P 11/025; B23P 19/02; B21D 39/046
See application file for complete search history.

(56) References Cited

U.S. PATENT DOCUMENTS

| | | |
|---|---|---|
| 5,261,263 A | 11/1993 | Whitesell |
| 5,556,383 A | 9/1996 | Wang et al. |
| 5,672,169 A | 9/1997 | Verbeek |
| 5,836,965 A | 11/1998 | Jendersee et al. |
| 5,913,871 A | 6/1999 | Werneth et al. |
| 5,976,181 A | 11/1999 | Whelan et al. |
| 5,992,000 A | 11/1999 | Humphrey et al. |
| 6,018,857 A | 2/2000 | Duffy et al. |

(Continued)

FOREIGN PATENT DOCUMENTS

| | | |
|---|---|---|
| CN | 1260213 | 7/2000 |
| CN | 101015440 | 8/2007 |

(Continued)

OTHER PUBLICATIONS

U.S. Appl. No. 11/330,927, filed Jan. 11, 2006, Wu et al.

(Continued)

*Primary Examiner* — Jermie E Cozart
(74) *Attorney, Agent, or Firm* — Squire Patton Boggs (US) LLP

(57) ABSTRACT

A medical device includes a balloon expanded scaffold crimped to a balloon catheter. The scaffold has a network of rings formed by struts connected at crowns and links connecting adjacent rings. The scaffold has a polymer coating and is crimped to the balloon. The scaffold is rotated, or allowed to rotate during crimping to improve results from crimping, such as reduced damage to the coating.

21 Claims, 15 Drawing Sheets

(56) References Cited

U.S. PATENT DOCUMENTS

| | | |
|---|---|---|
| 6,063,092 A | 5/2000 | Shin |
| 6,092,526 A | 7/2000 | LaFontaine et al. |
| 6,179,867 B1 | 1/2001 | Cox |
| 6,305,436 B1 | 10/2001 | Andersen et al. |
| 6,312,459 B1 | 11/2001 | Huang et al. |
| 6,360,577 B2 | 3/2002 | Austin |
| 6,488,688 B2 | 12/2002 | Lim et al. |
| 6,629,350 B2 | 10/2003 | Motsenbocker |
| 6,666,880 B1 | 12/2003 | Chiu et al. |
| 6,745,445 B2 | 6/2004 | Spilka |
| 6,783,542 B2 | 8/2004 | Eidenschink |
| 6,805,703 B2 | 10/2004 | McMorrow |
| 6,863,683 B2 | 3/2005 | Schwager et al. |
| 6,931,899 B2 | 8/2005 | Goff et al. |
| 7,010,850 B2 | 3/2006 | Hijlkema et al. |
| 7,156,869 B1 | 1/2007 | Pacetti |
| 7,316,148 B2 | 1/2008 | Asmus et al. |
| 7,389,670 B1 | 6/2008 | Kokish et al. |
| 7,563,400 B2 | 7/2009 | Wilson et al. |
| 7,648,727 B2 | 1/2010 | Hossainy et al. |
| 7,761,968 B2 | 7/2010 | Huang et al. |
| 7,762,804 B1 | 7/2010 | Stupecky |
| 7,763,198 B2 | 7/2010 | Knott et al. |
| 7,886,419 B2 | 2/2011 | Huang et al. |
| 7,945,409 B2 | 5/2011 | Furst et al. |
| 7,947,207 B2 | 5/2011 | McNiven et al. |
| 7,951,185 B1 | 5/2011 | Abbate et al. |
| 7,971,333 B2 | 7/2011 | Gale et al. |
| 8,002,817 B2 | 8/2011 | Limon |
| 8,046,897 B2 | 11/2011 | Wang et al. |
| 8,123,793 B2 | 2/2012 | Roach et al. |
| 8,225,474 B2 | 7/2012 | Arcand et al. |
| 8,261,423 B2 | 9/2012 | Jow et al. |
| 8,323,760 B2 | 12/2012 | Zheng et al. |
| 8,425,587 B2 | 4/2013 | Trollsas et al. |
| 8,539,663 B2 | 9/2013 | Wang et al. |
| 8,595,913 B2 | 12/2013 | Knott et al. |
| 8,726,483 B2 | 5/2014 | Stankus et al. |
| 8,752,261 B2 | 6/2014 | Van Sciver |
| 8,752,265 B2 | 6/2014 | Wang |
| 8,844,113 B2 | 9/2014 | Wang |
| 8,961,848 B2 | 2/2015 | Roberts et al. |
| 9,155,870 B2 | 10/2015 | Wang |
| 9,199,408 B2 | 12/2015 | Wang et al. |
| 9,283,100 B2 | 3/2016 | Wang et al. |
| 9,308,106 B2 | 4/2016 | Knott et al. |
| 9,642,729 B2 | 5/2017 | Wang et al. |
| 9,681,971 B2 | 6/2017 | Wang |
| 9,724,219 B2 | 8/2017 | Wang |
| 9,895,241 B2 | 2/2018 | Wang |
| 9,931,787 B2 | 4/2018 | Harrington et al. |
| 9,999,527 B2 | 6/2018 | Pacetti et al. |
| 2002/0035774 A1 | 3/2002 | Austin |
| 2002/0143382 A1 | 10/2002 | Hijlkema et al. |
| 2003/0070469 A1 | 4/2003 | Kokish |
| 2004/0078953 A1 | 4/2004 | Spilka |
| 2004/0096538 A1 | 5/2004 | Goff et al. |
| 2004/0106973 A1 | 6/2004 | Johnson |
| 2004/0138731 A1 | 7/2004 | Johnson |
| 2004/0181236 A1 | 9/2004 | Eidenschink et al. |
| 2004/0260379 A1 | 12/2004 | Jagger et al. |
| 2005/0119720 A1 | 6/2005 | Gale et al. |
| 2005/0143752 A1 | 6/2005 | Schwager et al. |
| 2005/0159802 A1 | 7/2005 | Furst et al. |
| 2005/0183259 A1 | 8/2005 | Eidenschink et al. |
| 2005/0188525 A1 | 9/2005 | Weber et al. |
| 2005/0229670 A1 | 10/2005 | Perreault |
| 2005/0244533 A1 | 11/2005 | Motsenbocker et al. |
| 2005/0283225 A1 | 12/2005 | Klisch |
| 2006/0004469 A1 | 1/2006 | Sokel |
| 2006/0047336 A1 | 3/2006 | Gale et al. |
| 2006/0100694 A1 | 5/2006 | Globerman |
| 2006/0116748 A1 | 6/2006 | Kaplan et al. |
| 2006/0123874 A1 | 6/2006 | Motsenbocker |
| 2006/0196073 A1 | 9/2006 | Parker |
| 2007/0006441 A1 | 1/2007 | McNiven et al. |
| 2007/0023974 A1 | 2/2007 | Wu |
| 2007/0204455 A1 | 9/2007 | Knott et al. |
| 2007/0259099 A1 | 11/2007 | Van Sciver |
| 2007/0271763 A1 | 11/2007 | Huang et al. |
| 2007/0282433 A1 | 12/2007 | Limon et al. |
| 2007/0289117 A1 | 12/2007 | Huang et al. |
| 2007/0293938 A1 | 12/2007 | Gale et al. |
| 2008/0016668 A1 | 1/2008 | Huang et al. |
| 2008/0033523 A1 | 2/2008 | Gale et al. |
| 2008/0033524 A1 | 2/2008 | Gale |
| 2008/0033526 A1 | 2/2008 | Atladottir et al. |
| 2008/0072653 A1 | 3/2008 | Gillick et al. |
| 2008/0127707 A1 | 6/2008 | Kokish et al. |
| 2008/0147164 A1 | 6/2008 | Gale et al. |
| 2008/0208327 A1 | 8/2008 | Rowe |
| 2008/0275537 A1 | 11/2008 | Limon |
| 2009/0001633 A1 | 1/2009 | Limon et al. |
| 2009/0088829 A1 | 4/2009 | Wang et al. |
| 2009/0105800 A1 | 4/2009 | Sabaria |
| 2009/0133817 A1 | 5/2009 | Sabaria |
| 2009/0228094 A1 | 9/2009 | Yan et al. |
| 2009/0282669 A1 | 11/2009 | von Oepen et al. |
| 2009/0287289 A1 | 11/2009 | Sagedahl et al. |
| 2009/0299452 A1 | 12/2009 | Eidenschink et al. |
| 2010/0004735 A1 | 1/2010 | Yang et al. |
| 2010/0025894 A1 | 2/2010 | Kleiner et al. |
| 2010/0063571 A1 | 3/2010 | Roach et al. |
| 2010/0115755 A1 | 5/2010 | Pacetti |
| 2010/0286758 A1 | 11/2010 | Berglund |
| 2010/0323091 A1 | 12/2010 | Castro et al. |
| 2011/0152905 A1 | 6/2011 | Eaton |
| 2011/0190872 A1 | 8/2011 | Anukhin et al. |
| 2011/0270383 A1 | 11/2011 | Jow et al. |
| 2011/0271513 A1 | 11/2011 | Wang |
| 2011/0307046 A1 | 12/2011 | Bourang et al. |
| 2012/0010693 A1 | 1/2012 | Van Sciver |
| 2012/0017416 A1 | 1/2012 | Wang et al. |
| 2012/0042501 A1 | 2/2012 | Wang et al. |
| 2012/0079706 A1 | 4/2012 | Knott et al. |
| 2012/0285609 A1 | 11/2012 | Wang |
| 2012/0316635 A1 | 12/2012 | Jow et al. |
| 2013/0255853 A1 | 10/2013 | Wang et al. |
| 2014/0033506 A1 | 2/2014 | Jow et al. |
| 2014/0096357 A1 | 4/2014 | Wang |
| 2014/0189994 A1 | 7/2014 | Van Sciver |
| 2014/0230225 A1 | 8/2014 | Van Sciver |
| 2014/0336747 A1 | 11/2014 | Rapoza et al. |
| 2015/0059960 A1 | 3/2015 | Roberts et al. |
| 2015/0257907 A1 | 9/2015 | Vial et al. |
| 2016/0081824 A1 | 3/2016 | Harrington et al. |
| 2017/0348124 A1 | 12/2017 | Wang |
| 2018/0116830 A1 | 5/2018 | Wang |
| 2018/0228630 A1 | 8/2018 | Wang et al. |

FOREIGN PATENT DOCUMENTS

| | | |
|---|---|---|
| EP | 0 787 020 | 8/1997 |
| EP | 1 000 591 | 5/2000 |
| EP | 1 226 798 | 7/2002 |
| EP | 1 295 570 | 3/2003 |
| EP | 1 818 073 | 8/2007 |
| EP | 2 029 052 | 3/2009 |
| JP | 2005-535459 | 11/2005 |
| JP | 2008-538940 | 11/2008 |
| JP | 2009-540928 | 11/2009 |
| JP | 2009-542263 | 12/2009 |
| JP | 2010-525903 | 7/2010 |
| JP | 2010-540091 | 12/2010 |
| WO | WO 99/55406 | 11/1999 |
| WO | WO 00/36994 | 6/2000 |
| WO | WO 01/35861 | 5/2001 |
| WO | WO 02/074192 | 9/2002 |
| WO | WO 02/102283 | 12/2002 |
| WO | WO 2004/016369 | 2/2004 |
| WO | WO 2005/053937 | 6/2005 |
| WO | WO 2006/110861 | 10/2006 |
| WO | WO 2006/117016 | 11/2006 |
| WO | WO 2007/116305 | 10/2007 |

(56) References Cited

FOREIGN PATENT DOCUMENTS

| WO | WO 2007/146354 | 12/2007 |
|----|----------------|---------|
| WO | WO 2007/146543 | 12/2007 |
| WO | WO 2007/149464 | 12/2007 |
| WO | WO 2008/011028 | 1/2008 |
| WO | WO 2008/033621 | 3/2008 |
| WO | WO 2008/137821 | 11/2008 |
| WO | WO 2009/045764 | 4/2009 |
| WO | WO 2010/036982 | 4/2010 |
| WO | WO 2010/151497 | 12/2010 |
| WO | WO 2011/136929 | 11/2011 |
| WO | WO 2012/006451 | 1/2012 |
| WO | WO 2012/027172 | 3/2012 |
| WO | WO 2012/044454 | 4/2012 |
| WO | WO 2013/039637 | 3/2013 |

OTHER PUBLICATIONS

U.S. Appl. No. 11/938,127, filed Nov. 9, 2007, Wang.
Angioplasty Summit Abstracts/Oral, Am J Cardiol. Apr. 23-26, 2013, p. 23B.
Bosiers et al., "Coronary and endovascular applications of the AbsorbTM bioresorbable vascular scaffold", Interv Cardiol. 2012; 4(6): 621-631.
Miller, R., "Abbott's Bioresorbable Stent Shows Durable Results in ABSORB Trial", The Gray Sheet, Mar. 25, 2013, pp. 17-18.
Zhang et al., "Heparin-and basic fibroblast growth factor-incorporated degradable stent: comparison with traditional transmyocardial revascularization", J Cardiovasc Surg. 2011; 52: 261-270.

ROTATION OF A MEDICAL DEVICE DURING CRIMPING

BACKGROUND OF THE INVENTION

Field of the Invention

The present invention relates to medical devices; more particularly, this invention relates to processes for reducing or avoiding damage to medical device coatings and surfaces caused by a crimping apparatus.

Description of the State of the Art

Radially expandable endoprostheses are artificial devices adapted to be implanted in an anatomical lumen. An "anatomical lumen" refers to a cavity, or duct, of a tubular organ such as a blood vessel, urinary tract, and bile duct. Stents are examples of endoprostheses that are generally cylindrical in shape and function to hold open and sometimes expand a segment of an anatomical lumen. Stents are often used in the treatment of atherosclerotic stenosis in blood vessels. "Stenosis" refers to a narrowing or constriction of the diameter of a bodily passage or orifice. In such treatments, stents hold open the walls of the blood vessel and prevent acute closure, vasospasm and restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The treatment of a diseased site or lesion with a stent involves both delivery and deployment of the stent. "Delivery" refers to introducing and transporting the stent through an anatomical lumen to a desired treatment site, such as a lesion. "Deployment" corresponds to expansion of the stent within the lumen at the treatment region. Delivery and deployment of a stent are accomplished by positioning the stent about one end of a catheter, inserting the end of the catheter through the skin into the anatomical lumen, advancing the catheter in the anatomical lumen to a desired treatment location, expanding the stent at the treatment location, and removing the catheter from the lumen.

The stent must be able to satisfy a number of basic, functional requirements. The stent (or scaffold) must be capable of sustaining radial compressive forces as it supports walls of a vessel. Therefore, a stent must possess adequate radial strength. After deployment, the stent must adequately maintain its size and shape throughout its service life despite the various forces that may come to bear on it. In particular, the stent must adequately maintain a vessel at a prescribed diameter for a desired treatment time despite these forces. The treatment time may correspond to the time required for the vessel walls to remodel, after which the stent is no longer needed.

Scaffolds may be made from a biodegradable, bioabsorbable, bioresorbable, or bioerodable polymer. The terms biodegradable, bioabsorbable, bioresorbable, biosoluble or bioerodable refer to the property of a material or stent to degrade, absorb, resorb, or erode away from an implant site. Scaffolds may also be constructed of bioerodible metals and alloys. The scaffold, as opposed to a durable metal stent, is intended to remain in the body for only a limited period of time. In many treatment applications, the presence of a stent in a body may be necessary for a limited period of time until its intended function of, for example, maintaining vascular patency and/or drug delivery is accomplished. Moreover, it has been shown that biodegradable scaffolds allow for improved healing of the anatomical lumen as compared to metal stents, which may lead to a reduced incidence of late stage restenosis and thrombosis. In these cases, there is a desire to treat a vessel using a polymer scaffold, in particular a bioabsorbable or bioresorbable polymer scaffold, as opposed to a metal stent, so that the prosthesis's presence in the vessel is temporary.

Polymeric materials considered for use as a polymeric scaffold, e.g. poly(L-lactide) ("PLLA"), poly(D,L-lactide-co-glycolide) ("PDLLA-co-GA"), poly(D-lactide-co-glycolide) or poly(L-lactide-co-D-lactide) ("PLLA-co-PDLA") with less than 10% D-lactide, poly(L-lactide-co-caprolactone), poly(caprolactone), PLLA/PDLA stereo complex, and blends of the aforementioned polymers may be described, through comparison with a metallic material used to form a stent, in some of the following ways. Polymeric materials typically possess a lower strength to volume ratio compared to metals, which means more material is needed to provide an equivalent mechanical property. Therefore, struts must be made thicker and wider to have the required strength for a stent to support lumen walls at a desired radius. The scaffold made from such polymers also tends to be less ductile or have limited fracture toughness. The anisotropic and rate-dependent inelastic properties (i.e., strength/stiffness of the material varies depending upon the rate at which the material is deformed, in addition to the temperature, degree of hydration, thermal history) inherent in the material, only compound this complexity in working with a polymer, particularly bioresorbable polymers such as PLLA or PDLLA-co-GA.

Scaffolds and stents traditionally fall into two general categories—balloon expanded and self-expanding. The latter type expands (at least partially) to a deployed or expanded state within a vessel when a radial restraint is removed, while the former relies on an externally-applied force to configure it from a crimped or stowed state to the deployed or expanded state.

Self-expanding stents are designed to expand significantly when a radial restraint is removed such that a balloon is often not needed to deploy the stent. Self-expanding stents do not undergo, or undergo relatively little plastic or inelastic deformation when stowed in a sheath or expanded within a lumen (with or without an assisting balloon). Balloon expanded stents or scaffolds, by contrast, undergo a significant plastic or inelastic deformation when both crimped and later deployed by a balloon.

In the case of a balloon expandable stent, the stent is mounted about a balloon portion of a balloon catheter. The stent is compressed or crimped onto the balloon. Crimping may be achieved by use of an iris or sliding-wedge types, or other types of crimping mechanisms. A significant amount of plastic or inelastic deformation occurs both when the balloon expandable stent or scaffold is crimped and later deployed by a balloon. At the treatment site within the lumen, the stent is expanded by inflating the balloon. The expanded state is achieved and maintained, substantially, if not entirely by an irreversible or inelastic strain at the crowns (or crests) of the stent or scaffold caused by the balloon expansion. Self-expanding stents or scaffolds, by contrast, achieve and maintain their expanded state in the vessel by an elastic, radially outward force.

Methods of mounting an intravascular device (stent, scaffold, tube, etc.) on a balloon catheter frequently involves positioning the device on a balloon dilatation catheter, collapsing the jaws around the device until a radially compressive force is applied on the outer surface of the stent, thereby decreasing the outer diameter of the stent on the balloon catheter. The balloon can be heated and pressurized for a number of cycles wherein the balloon expands into the stent gaps to embed the stent in an outer surface of the balloon. The stent may be restrained from radially expanding by using a mold, for example a split mold, or a sheath. The balloon may further expand into the stent gaps to more securely embed the stent in an outer surface of the balloon until the stent reaches its final crimped diameter.

Present day crimping manufacturers generally place emphasis on the jaws themselves—with added technology that allows the use of optional film, media or material to protect, lubricate or envelope the device during each respective crimping stage. Advances can also include crimper jaws made of different materials which have different hardness or non-stick properties. The number, dimension and shape of jaws can be tailored depending on the device morphology to be crimped. However, all crimpers also affix or stabilize the catheter that the stent is being crimped onto. These fixtures or stabilization platforms are designed to hold the catheter in-place while the crimping operation is performed. They are engineered to be easy to use so that the catheter can be affixed and removed easily.

For example, a film-head crimper has been used to crimp stents onto balloons. Referring to FIG. 1A, there is shown a perspective view of a crimping assembly 20 that includes three rolls 123, 124, 125 used to position a clean sheet of non-stick material between the crimping blades and the stent prior to crimping. For example, upper roll 125 holds the sheet secured to a backing sheet. The sheet is drawn from the backing sheet by a rotating mechanism (not shown) within the crimper head 20. A second sheet is dispensed from the mid roll 124. After crimping, the first and second (used) sheets are collected by the lower roll 123. As an alternative to rollers dispensing a non-stick sheet, a stent may be covered in a thin, compliant protective sheath before crimping.

FIG. 1B illustrates the positioning the first sheet 125a and second sheet 124a relative to the wedges 22 and a stent 100 within the aperture of the crimper head 20. As illustrated each of the two sheets are passed between two blades 22 on opposite sides of the stent 100 and a tension T1 and T2 applied to gather up excess sheet material as the iris of the crimping assembly is reduced in size via the converging blades 22.

The dispensed sheets of non-stick material (or protective sheath) are primarily used to avoid buildup of coating material on the crimper blades for stents coated with a therapeutic agent. The sheets 125a, 124a are replaced by a new sheet after each crimping sequence. By advancing a clean sheet after each crimp, accumulation of contaminating coating material from previously crimped stents is avoided. This eliminates transfer of accumulated drug and particulates to subsequent stents. By using replaceable sheets, stents having different drug coatings can be crimped using the same crimping assembly without risk of contamination or buildup of coating material from prior stent crimping.

There is a continuing need to improve upon methods for crimping a medical device and, in particular, a stent or scaffold having a drug-polymer coating that may become damaged during crimping.

SUMMARY OF THE INVENTION

The invention provides an improved method and apparatus for crimping a balloon-expanded stent or scaffold to a balloon catheter. The stent or scaffold has a drug-polymer, or polymer coating. The method and apparatus relate to a crimping process that includes rotating, or allowing a balloon catheter to rotate about an aperture axis of the crimper head (the Y-axis illustrated in FIG. 3A) while the stent or scaffold is crimped to the balloon of the balloon catheter. The rotation of the balloon catheter during crimping reduces any torque applied to the stent or scaffold surface. When this torque inherent in a sliding-wedge or iris-type crimping mechanism was reduced or eliminated, there was also a significant reduction in shearing stress applied to the stent or scaffold coating during crimping. The reduced shear stress resulted in less damage to the coating after crimping. Embodiments of methods and apparatus are summarized below, followed by detailed descriptions of each.

A crimping process according to one aspect proceeds in stages. Between one or more, or all of the stages in a crimping process where there is a diameter reduction, the catheter may be supported within a loading stage (e.g., a channel or grooved member configured to place the catheter within the crimper), which aligns the catheter distal end with the aperture axis of the crimper. The loading stage may be supported on a bearing, which allows rotation about the Y-axis. The loading stage may also be connected to a motor that is arranged to rotate the loading stage about the Y-axis.

According to the various aspects of the invention, there is a coated stent or scaffold, medical device, method for crimping the stent or scaffold, a balloon catheter, crimping device, or method for assembly of a medical device comprising such a stent, scaffold, balloon catheter and using the crimping device having one or more, or any combination of the following things (1) through (15):

(1) A stent or scaffold to be crimped using a crimping device;

(2) A balloon catheter on which the stent or scaffold will be crimped;

(3) A film head crimper with or without bearings to allow crimp head to rotate about Y axis;

(4) A crimping apparatus wherein a catheter support, e.g., stage including a tray, is supported on bearings that permit rotation of the catheter support (and catheter) about the Y axis;

(5) A crimping apparatus wherein a catheter is supported on a flat surface to allow for free rotation about the Y axis and/or translation of a crimping shaft during a crimping process;

(6) A crimping apparatus wherein the catheter is supported by an inertia-balanced support so that there is a minimal amount of gravity-induced Y axis torque caused by the support during crimping;

(7) A crimping apparatus wherein a catheter is supported on a flat surface to allow for free rotation and/or translation of a crimping shaft during a crimping process;

(8) A crimping apparatus open-loop torque control wherein a support for the catheter is coupled to a motor and the motor applies a predefined torque derived from blade kinematics and rate of diameter reduction by crimp head;

(9) A torque-less crimping apparatus wherein the crimp head is mounted on rotational bearings to counter-act any torque caused by crimping blades bearing down on scaffold;

(10) A method, comprising: using a stent or scaffold, the stent or scaffold having an outer diameter and the outer diameter having a before crimping size; using a balloon of a balloon catheter; using a crimping device having a plurality of blades configured to form an aperture, wherein the blades are displaced relative to each other to increase or decrease the size of the aperture during crimping, and wherein the aperture has an axis surrounded by the blades; and crimping the stent or scaffold to the balloon, the crimping comprising: placing the stent or scaffold on the balloon, aligning the stent or scaffold and balloon catheter with the aperture axis, including supporting the balloon catheter using a bearing having a bearing axis parallel to the aperture axis, and reducing the stent or scaffold outer diameter from the before crimping size to a first size;

(11) The method of (10) or apparatus described herein according to one or more, or any combination of the following things a) through l):
  a) wherein the crimping device is a film-head crimper;
  b) wherein when the blades of crimping device rotate about the aperture axis when the aperture size changes, whereupon the catheter rotates about the bearing axis in response to the rotation of the blades about the aperture axis;
  c) wherein the crimping further includes the step of reducing the stent or scaffold outer diameter from the first size to a second size, and rotating the catheter about the bearing axis while the stent or scaffold outer diameter is reduced from the first size to a second size;
  d) wherein the second size is at least 50% of the before crimping size;
  e) wherein the catheter is rotated using a motor;
  f) wherein the motor is a stepper motor;
  g) wherein the motor rotates the catheter by an angle of between about 2 degrees and about 50 degrees;
  h) wherein the motor rotates the catheter by no more than about 26 degrees;
  i) wherein the crimping device includes polymer material disposed between the blades and the stent or scaffold during the crimping, wherein the polymer material is re-set within the aperture before or after the rotating the catheter about the bearing axis while the stent or scaffold outer diameter is reduced from the first size to a second size;
  j) wherein before or after reducing the scaffold diameter from the first size to the second size the aperture is held constant;
  k) wherein the catheter is rotated after the stent or scaffold diameter is reduced to 50% or less than 50% of the before crimping diameter; and/or
  l) wherein the crimping step crimps a scaffold to the balloon, and the balloon has a nominal inflation diameter, and wherein the before crimping size is greater than a nominal diameter of the balloon, the scaffold is made from a tube comprising a polymer, the polymer having a glass transition temperature, and the scaffold is subjected to a crimping temperature during the crimping;

(12) An apparatus, comprising: a crimp head having an opening and a plurality of blades defining an aperture and aperture axis, wherein the blades are rotated about the aperture axis to increase or decrease the size of the aperture; and a loading stage mounted on a surface adjacent the opening, the loading stage comprising a channel aligned with the aperture axis, and a bearing having a bearing axis and supporting the channel above the surface, wherein the bearing axis is coincident with the aperture axis;

(13) The method of (10) or described herein, or apparatus of (12) according to one or more, or any combination of the following things a) through d):
  a) wherein the loading stage is coupled to a first motor for displacing the loading stage along the aperture axis, towards or away from the opening;
  b) wherein the loading stage is coupled to a second motor for rotating the loading stage about the bearing axis;
  c) wherein the second motor is a stepper motor; and/or
  d) A method for crimping a medical device to a balloon catheter using the apparatus of 12, wherein the balloon catheter is held by the loading stage during the crimping;

(14) A method, comprising: using a stent or scaffold, the stent or scaffold having an outer diameter and the outer diameter having a before crimping size; using a balloon of a balloon catheter; using a crimping device having an opening and a plurality of blades defining an aperture and aperture axis, wherein the blades are rotated about the aperture axis to increase or decrease the size of the aperture; and crimping the stent or scaffold to the balloon, the crimping comprising: placing the stent or scaffold on the balloon, and reducing the stent or scaffold outer diameter from the before crimping size to a first size, wherein when the blades rotate about the aperture axis to reduce the stent or scaffold outer diameter, the balloon catheter rotates using a means for rotating;

(15) The method of (10) or (14), or apparatus of (12) according to one or more, or any combination of the following things a) through c):
  a) wherein the means for rotating is at least one of a bearing supporting the catheter and a motor coupled to a channel that supports the catheter;
  b) further comprising a controlled heating element to set the blades to temperature; and/or
  c) wherein the method is performed while the heating element warms the stent or scaffold.

INCORPORATION BY REFERENCE

All publications and patent applications mentioned in the present specification are herein incorporated by reference to the same extent as if each individual publication or patent application was specifically and individually indicated to be incorporated by reference. To the extent there are any inconsistent usages of words and/or phrases between an incorporated publication or patent and the present specification, these words and/or phrases will have a meaning that is consistent with the manner in which they are used in the present specification.

DETAILED DESCRIPTION

Figure 1A:
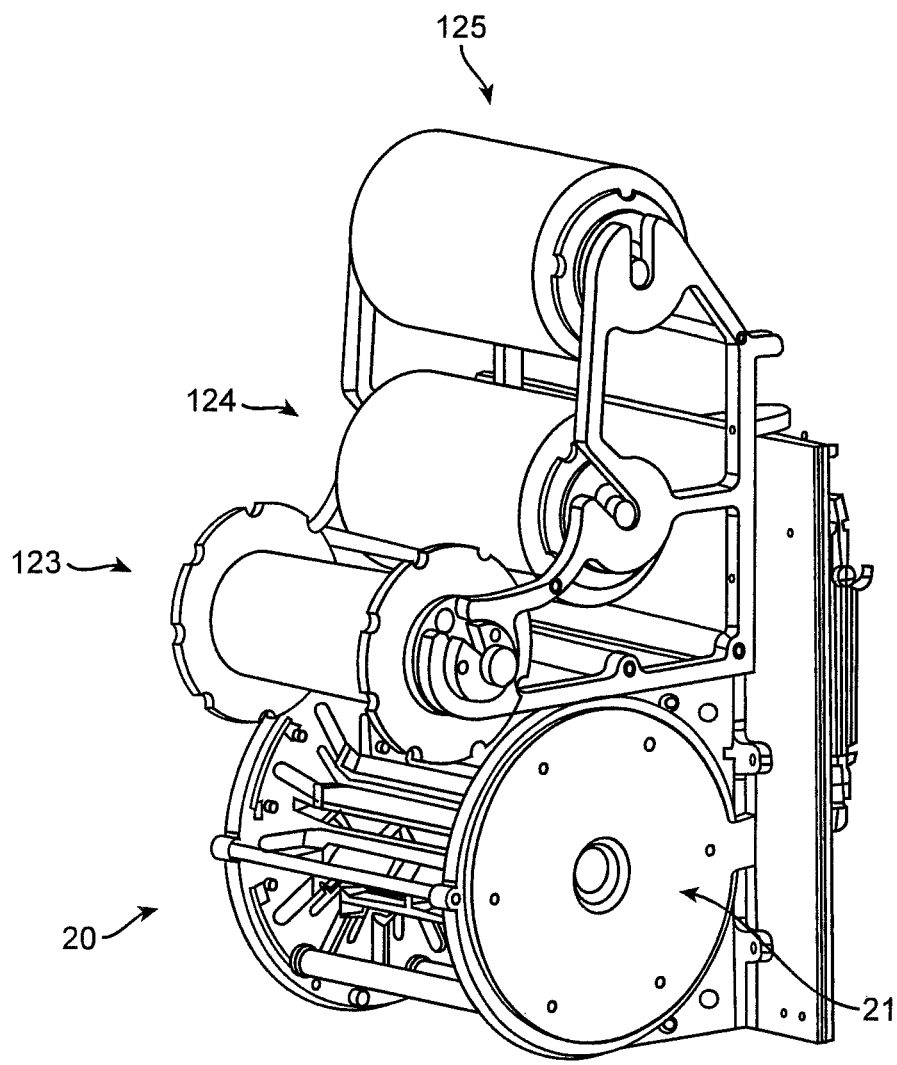
FIG. 1A is a perspective view of a prior art film-head crimper.

In the description like reference numbers appearing in the drawings and description designate corresponding or like elements among the different views.

For purposes of this disclosure, the following terms and definitions apply:

The terms "about," "approximately," "generally," or "substantially" mean 30%, 20%, 15%, 10%, 5%, 4%, 3%, 2%, 1.5%, 1%, between 1-2%, 1-3%, 1-5%, or 0.5%-5% less or more than, less than, or more than a stated value, a range or each endpoint of a stated range, or a one-sigma, two-sigma, three-sigma variation from a stated mean or expected value (Gaussian distribution). For example, d1 about d2 means d1 is 30%, 20%, 15%, 10%, 5%, 4%, 3%, 2%, 1.5%, 1%, 0% or between 1-2%, 1-3%, 1-5%, or 0.5%-5% different from d2. If d1 is a mean value, then d2 is about d1 means d2 is within a one-sigma, two-sigma, or three-sigma variance or standard deviation from d1.

It is understood that any numerical value, range, or either range endpoint (including, e.g., "approximately none", "about none", "about all", etc.) preceded by the word "about," "approximately," "generally," or "substantially" in this disclosure also describes or discloses the same numerical value, range, or either range endpoint not preceded by the word "about," "approximately," "generally," or "substantially."

The "glass transition temperature," Tg, is the temperature at which the amorphous domains of a polymer change from a brittle vitreous state to a solid deformable or ductile state at atmospheric pressure. This application defines Tg and methods to find Tg, or Tg-low (the lower end of a Tg range) for a polymer in the same way as in U.S. application Ser. No. 14/857,635.

A "stent" means a permanent, durable or non-degrading structure, usually comprised of a non-degrading metal or metal alloy structure, generally speaking, while a "scaffold" means a temporary structure comprising a bioresorbable or biodegradable polymer, metal, alloy or combination thereof and capable of radially supporting a vessel for a limited period of time, e.g., 3, 6 or 12 months following implantation. It is understood, however, that the art sometimes uses the term "stent" when referring to either type of structure.

"Inflated diameter" or "expanded diameter" refers to the inner diameter or the outer diameter the scaffold attains when its supporting balloon is inflated to expand the scaffold from its crimped configuration to implant the scaffold within a vessel. The inflated diameter may refer to a post-dilation balloon diameter which is beyond the nominal diameter, or nominal inflated diameter for the balloon (e.g., a 6.5 mm balloon has a nominal diameter of 6.5 mm or when inflated to its nominal inflated diameter has a diameter of 6.5 mm). The scaffold diameter, after attaining its inflated or expanded diameter by balloon pressure, will to some degree decrease in diameter due to recoil effects related primarily to, any or all of, the manner in which the scaffold was fabricated and processed, the scaffold material and the scaffold design. When reference is made to a fully inflated diameter of a balloon, it refers to balloon pressurization corresponding to the nominal inflated diameter or greater than the nominal inflated diameter.

When reference is made to a diameter it shall mean the inner diameter or the outer diameter, unless stated or implied otherwise given the context of the description.

"Post-dilation diameter" (PDD) of a scaffold refers to the inner diameter of the scaffold after being increased to its expanded diameter and the balloon removed from the patient's vasculature. The PDD accounts for the effects of recoil. For example, an acute PDD refers to the scaffold diameter that accounts for an acute recoil in the scaffold.

A "before-crimp diameter" means an outer diameter (OD) of a tube from which the scaffold was made (e.g., the scaffold is cut from a dip coated, injection molded, extruded, radially expanded, die drawn, and/or annealed tube) or the scaffold before it is crimped to a balloon. Similarly, a "crimped diameter" means the OD of the scaffold when crimped to a balloon. The "before-crimp diameter" can be about 2 to 2.5, 2 to 2.3, 2.3, 2, 2.5, 3.0 times greater than the crimped diameter and about 0.9, 1.0, 1.1, 1.3 and about 1-1.5 times higher than an expanded diameter, the nominal balloon diameter, or post-dilation diameter. Crimping, for purposes of this disclosure, means a diameter reduction of a scaffold characterized by a significant plastic deformation, i.e., more than 10%, or more than 50% of the diameter reduction is attributed to plastic deformation, such as at a crown (or crest) in the case of a stent or scaffold that has an undulating ring pattern, e.g., FIG. 6. When the scaffold is deployed or expanded by the balloon, the inflated balloon plastically deforms the scaffold from its crimped diameter. Examples of methods of crimping scaffolds are described in US20130255853 and US20140096357.

A "crimping stage" or "stage" of a crimping process refers to a period of time when the jaws of a crimping device are held fixed, or the aperture of the crimp head is held at a constant diameter. The duration of the stage may be called a dwell period. Dwell periods can range from 1 to 25 seconds for the stages prior to the final dwell/stage. When the final crimped diameter is reached the dwell period may be between 50 sec and 300 seconds. The aperture of a crimping device is reduced from a first diameter to a second diameter when the crimping device moves from a first stage to a second stage, respectively. The aperture reduction sizes—e.g., from a first diameter or aperture size to second diameter or aperture size—are, for purposes of this disclosure, understood as being the same as the actual outer diameter of the scaffold within the aperture (correcting for a film, if present) when the scaffold is being reduced in size by the crimper. It is understood, however, that a programmed aperture size may not be exactly the same as the outer diameter of the crimped scaffold size, especially when a scaffold is being crimped to very small diameters.

A material "comprising" or "comprises" poly(L-lactide) or PLLA includes, but is not limited to, a PLLA polymer, a blend or mixture including PLLA and another polymer, and a copolymer of PLLA and another polymer. Thus, a strut comprising PLLA means the strut may be made from a material including any of a PLLA polymer, a blend or mixture including PLLA and another polymer, and a copolymer of PLLA and another polymer.

A "crimping temperature" according to the disclosure means a temperature above ambient and slightly less than, or about equal to the glass transition temperature (Tg) for a polymer of the scaffold, e.g., poly(L-lactide). In a preferred embodiment the crimping temperature is between Tg and 15 degrees less than Tg, or between Tg and 10 degrees, or 5 degrees less than Tg. In other embodiments the crimping temperature is achieved by heating the scaffold to a temperature at least 20 degrees below Tg and preferably to a temperature at least 15 degrees below Tg.

Figure 5A:
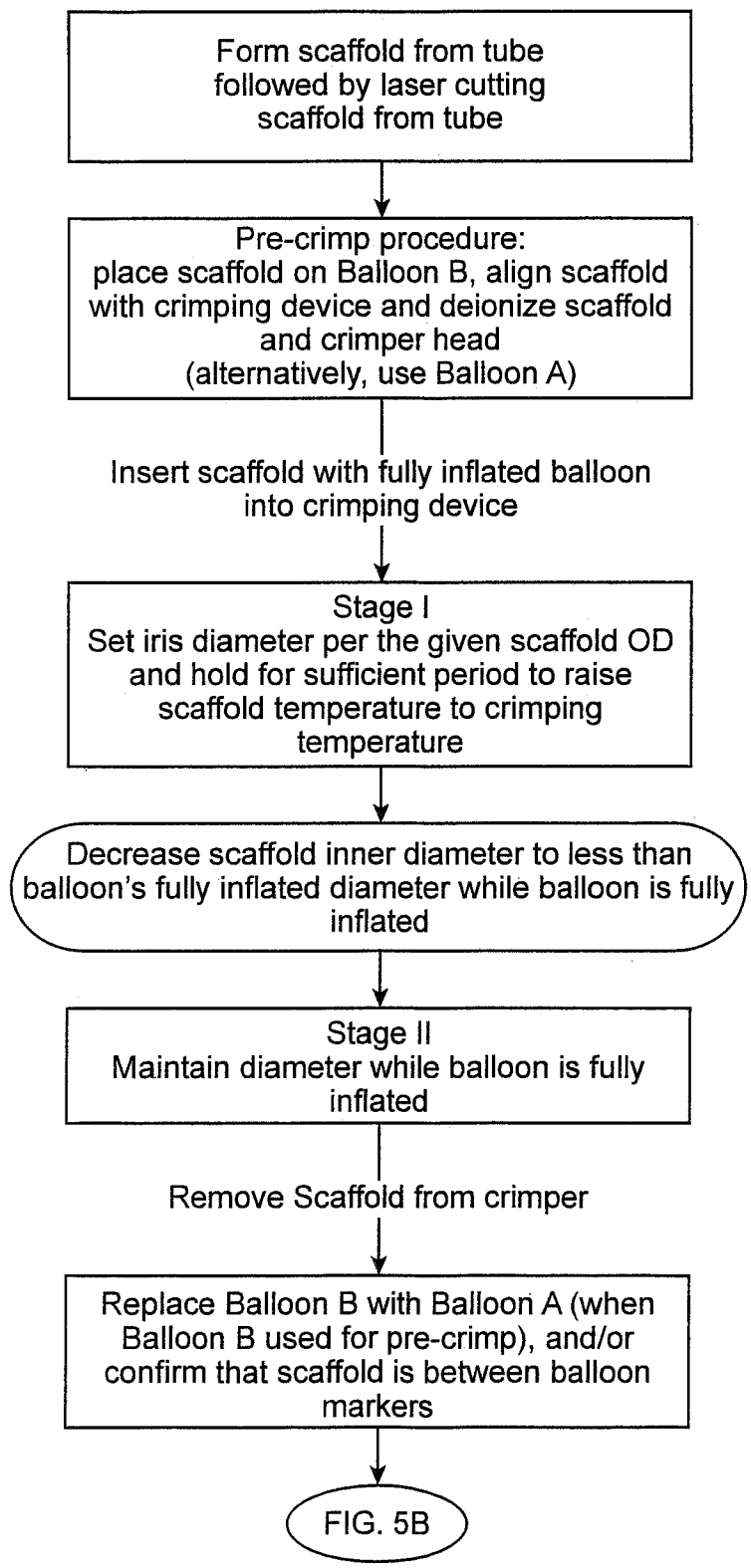
FIGS. 5A and 5B describe a crimping process for crimping a scaffold according to the disclosure.
Figure 5B:
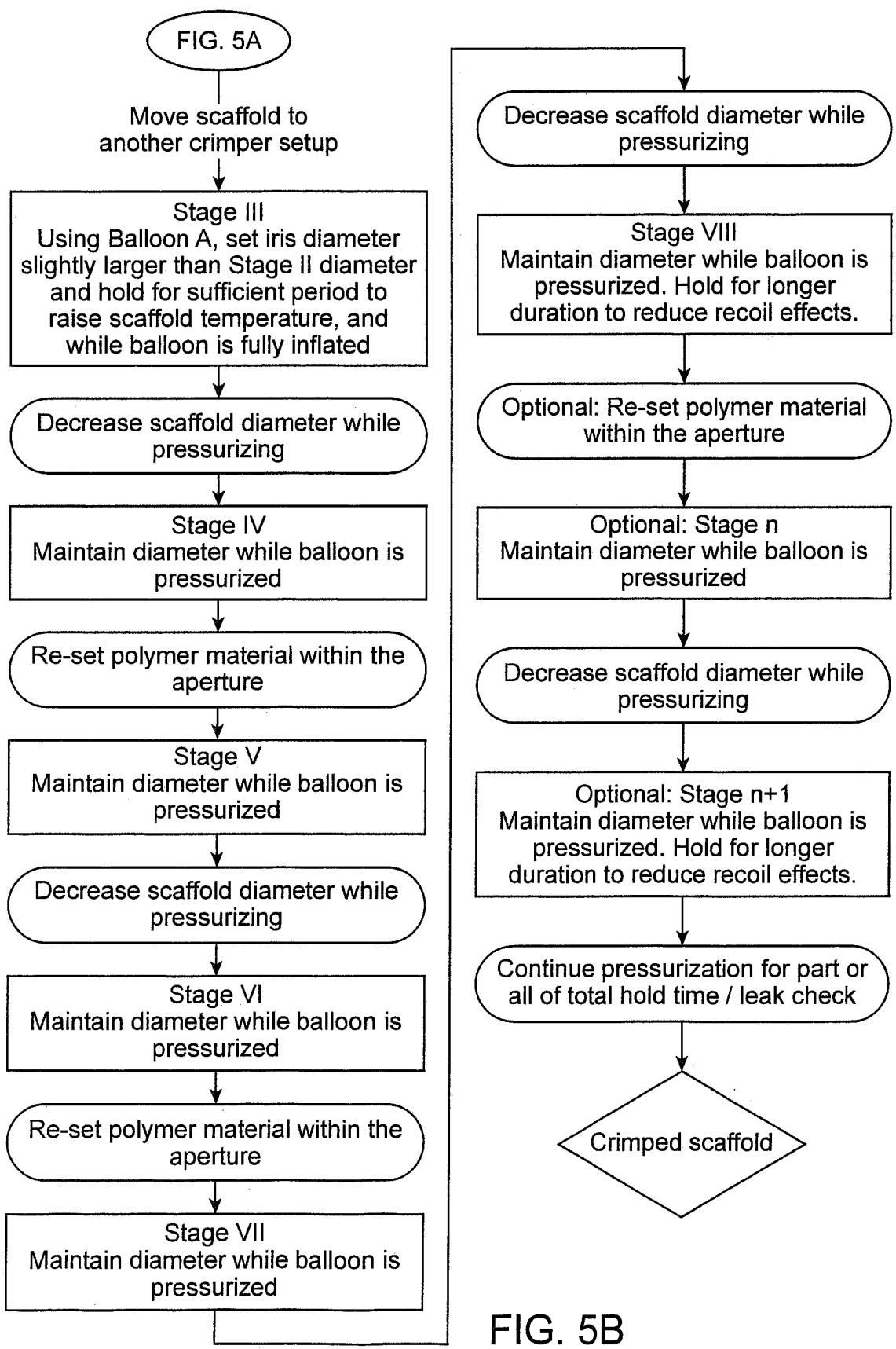

"Re-set of the polymer material within the aperture" as indicated in the crimping steps in FIG. 5B or "resetting of the polymer material within the aperture" means opening the aperture sufficiently to remove blade pressure on the scaffold to thereby allow removal of excess polymer material accumulated between the blades and scaffold during crimping. For example, where a film-head crimper is used, the excess polymer is excess polymer sheet material. The aperture is opened to re-tension the sheets, which removes the excess sheet material. In another example, the excess polymer material refers to a sheath that is too big relative to the scaffold diameter. The aperture is opened, the scaffold is removed from the crimper head and the existing sheath is replaced with a smaller diameter sheath. An example of a film-head crimper is the MSI™ SC775S/875S, available from the Machine Solutions Company. For this particular commercial crimper re-set of the polymer material (i.e., re-tensioning the sheets) within the aperture is accomplished by fully opening the crimp aperture.

A "bearing support" (or "bearing"), for purposes of this disclosure, is a structure that supports another structure (e.g., a catheter or channel for holding a catheter) by restraining translational motion of the other structure in one, two or three translational directions, and allowing free-rotation of the structure (relative to the bearing support) about only one axis—a bearing axis. An example of a bearing support is an inner and outer race with ball bearings held within the races. Alternatively, a bearing support is a frictionless, annular collar, or bushing configured to receive the structure. The collar or bushing restricts translation in two or three axes, but allows free rotation about the collar's or bushing's bearing axis. Or the inner surface of the collar or bushing may include a groove to receive a matching rib formed on the channel so that the collar/bushing permits rotation about the Y-axis, but not translation along the Y-axis. Magnetic bearings or air bearings are also possible for bearing supports.

A "bearing axis" means the axis of free translation and/or rotation provided by a bearing support, e.g. a loading stage of a crimping apparatus. For purposes of this disclosure, the bearing axis is parallel to the Y-axis, or aperture axis of the crimp head. For instance, the bearing axis for a ring bearing having an inner race, outer race, and ball bearings is the axis passing through the center of the ring. Or the bearing axis for a frictionless collar (i.e., a circular collar with inner walls covered by a low friction material, such as silicon) is the axis that passes through the geometric center of the collar.

Embodiments

An effective crimping process for a scaffold must at least satisfy each of the following objectives:
Structural integrity maintained: crimping minimizes damage to the scaffold backbone and/or coating as a result of crimping blades compressing the scaffold.
Safe delivery: crimping produces retention force sufficient to avoid dislodgement or separation of the scaffold from the balloon during delivery to an implant site.
Uniformity of expansion: crimping process avoids non-uniform expansion of scaffold rings at implant site.
Crimped Profile Adequate for Vascular Deliverability: Profile or diameter of the crimped scaffold is suitable for delivery in tight, tortuous anatomy.

The first objective, damage avoidance, refers to avoiding excessive stress buildup in struts or crowns (or crests) leading to fracture or crack propagation in struts, and out of plane twisting of struts. Damage avoidance also refers to damage to the coating. US20120042501 discusses these effects on a polymeric scaffold. The damage originates with the manner in which blades of a crimping mechanism operate to compress a scaffold diameter from a pre-crimp diameter to a final, or post-crimp diameter.

A common type of crimper is sometimes called a "sliding wedge" type of crimper. The mechanism forming the crimp aperture includes a series of wedges, or jaws arranged circumferentially around a central bore. The wedges are hinged together and attached to an actuator at their outer radius. When the actuator moves, the wedges rotate to increase or decrease the size of the crimp aperture. The scaffold, or scaffold and balloon (e.g., a balloon of a balloon catheter) is positioned at the geometric center of the crimp aperture and supported on a cantilevered support rod (e.g., the mandrel). The actuator moves the blades in unison to decrease the size of the aperture and bring blade surfaces to bear against the surface of the scaffold, thereby imposing radial compressive forces on the scaffold to reduce its diameter. Ideally, only these normal (i.e., radial) forces are imposed on the scaffold surfaces. The sliding-wedge mechanism however by its nature also applies a tangential or shear force because the blades are moving both radially towards the scaffold surface and rotating about the central axis of the aperture when the aperture is decreased in size. As such, when blades contact surfaces of the scaffold there is both a normal force and shear force applied to the scaffold surface. The net effect of these forces is an applied torque on the scaffold, i.e., a torque about the longitudinal axis (Y-axis) of the mandrel or balloon catheter.

The applied torque should cause the scaffold to rotate with the blades' rotation about the Y-axis. But while the scaffold itself is not purposely or directly restrained in rotation about the Y-axis, the catheter shaft upon which it is crimped is fixed in Y-axis rotation (all known crimping mechanisms fix the catheter shaft in Y-axis rotation). As such, any frictional resistance to Y-axis rotation of the scaffold relative to the balloon will produce a shearing stress on the abluminal surfaces of the scaffold. While this frictional resistance to Y-axis rotation may be minimal at the start of the crimping process, as the scaffold is pressed into the balloon surfaces the frictional resistance increases significantly to the point where, effectively, the scaffold becomes fixed in Y-axis rotation like the catheter shaft. When this happens a significant shear stress can develop and damage the coating on the scaffold surface.

Intravascular devices, such as a polymeric scaffold, may be coated with a drug, drug/polymer blend, polymeric-drug, therapeutic multi-material delivery layer. The aforementioned coating damage can be due to the shearing forces, as well as the normal forces from the blades. Damaged coating, including indentations or delamination leading to adhesion to the crimper jaws or polymer sheet, can impact drug release characteristics and material properties. It can also add surface roughness and irregularities if the coating becomes lifted and redistributed. Dislodged or missing coating may also increase the acute thrombogenicity of the stent when deployed in an arterial lumen.

Figure 1B:
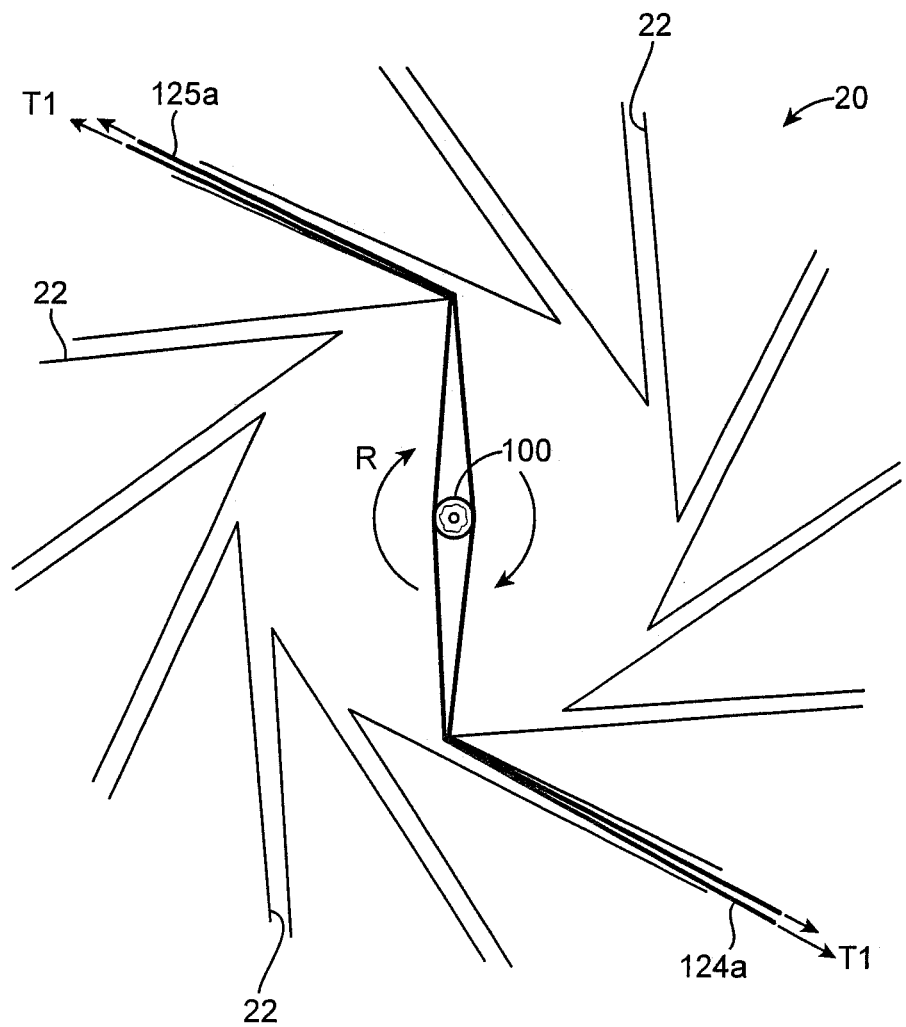
FIG. 1B is a frontal view of the head of the film-head crimper of FIG. 1A as crimper jaws are being brought down on a stent.
Figure 2A:
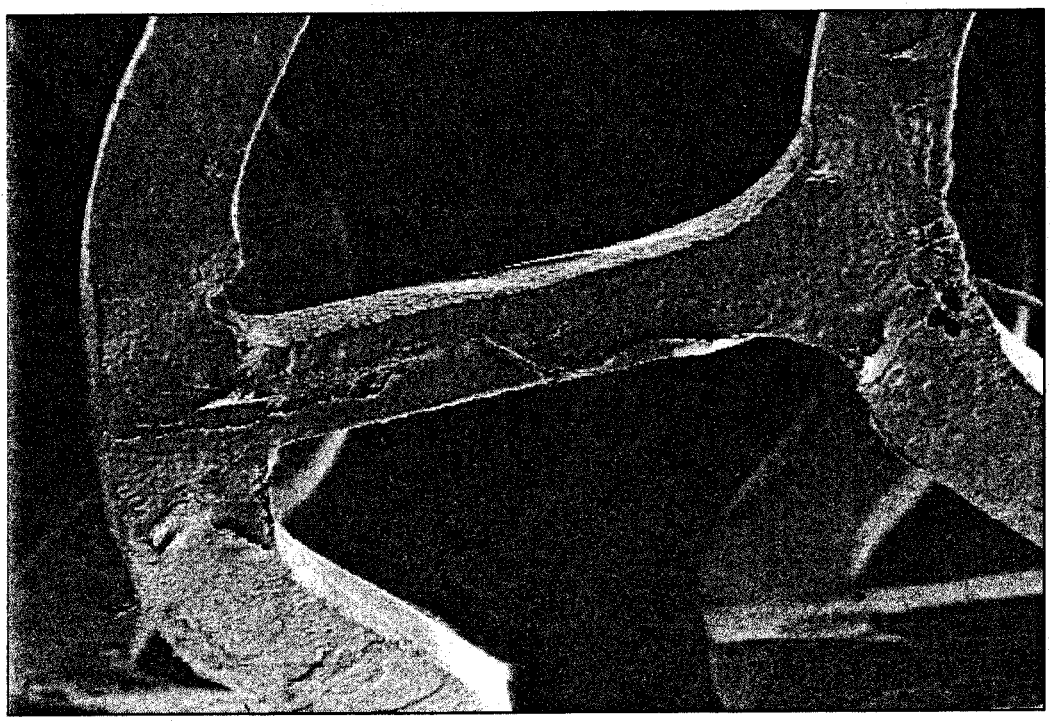
FIGS. 2A, 2B, 2C, 2D and 2E are photos reproduced from Scanning Electronic Microscope (SEM) images of abluminal surfaces of scaffolds crimped using a film-head crimper. The photos show damage to a coating on the scaffold.
Figure 2B:
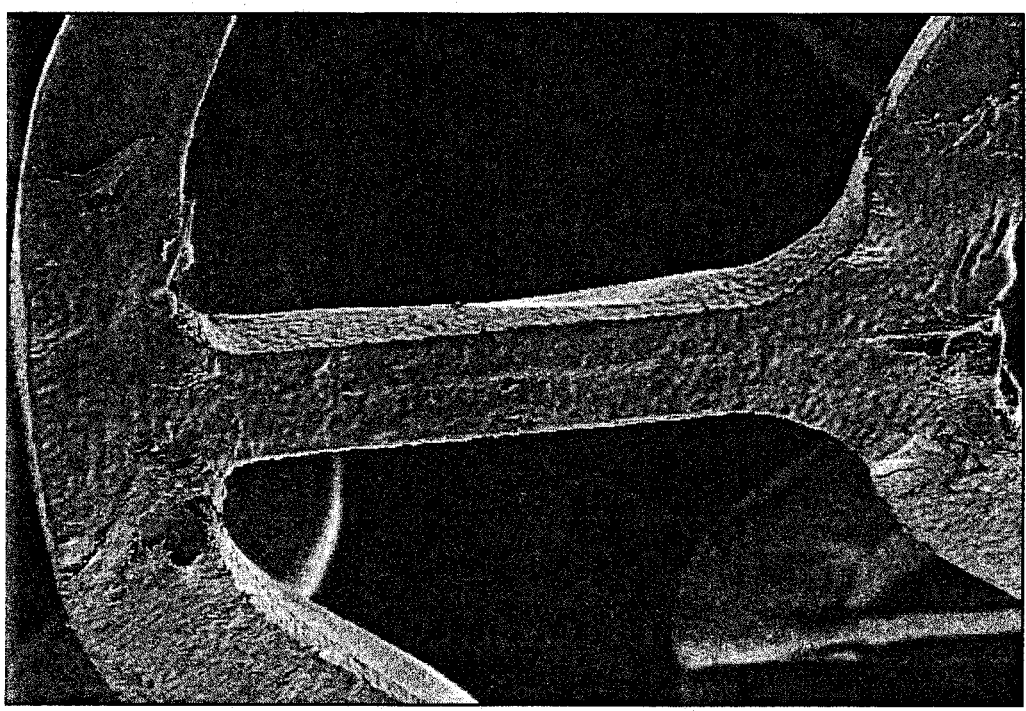
Figure 2C:
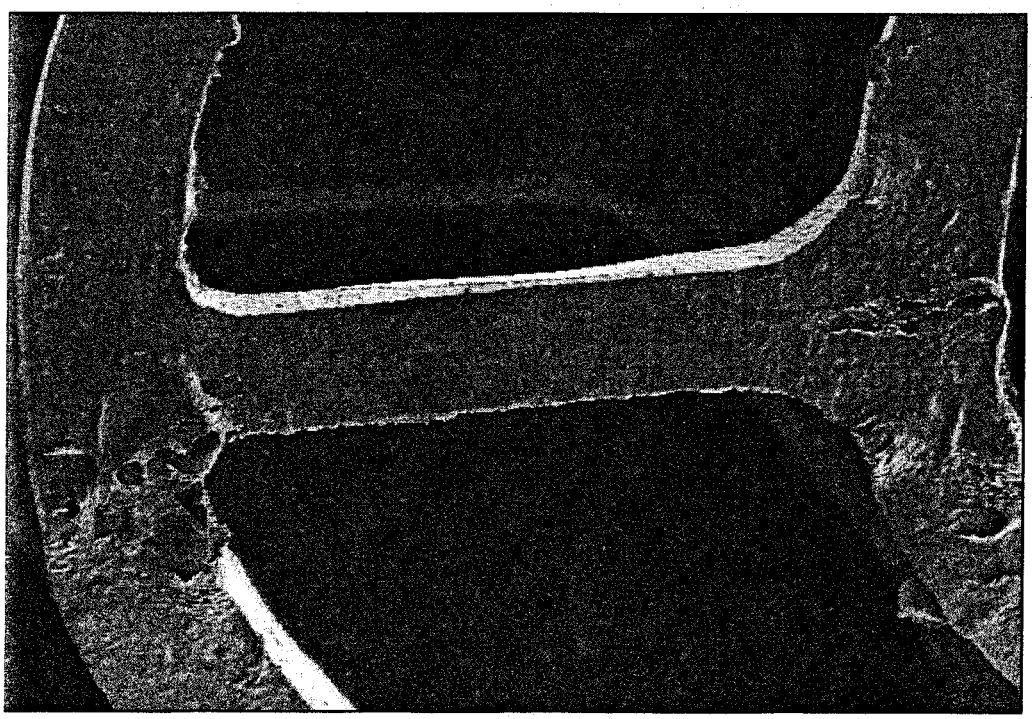
Figure 2D:
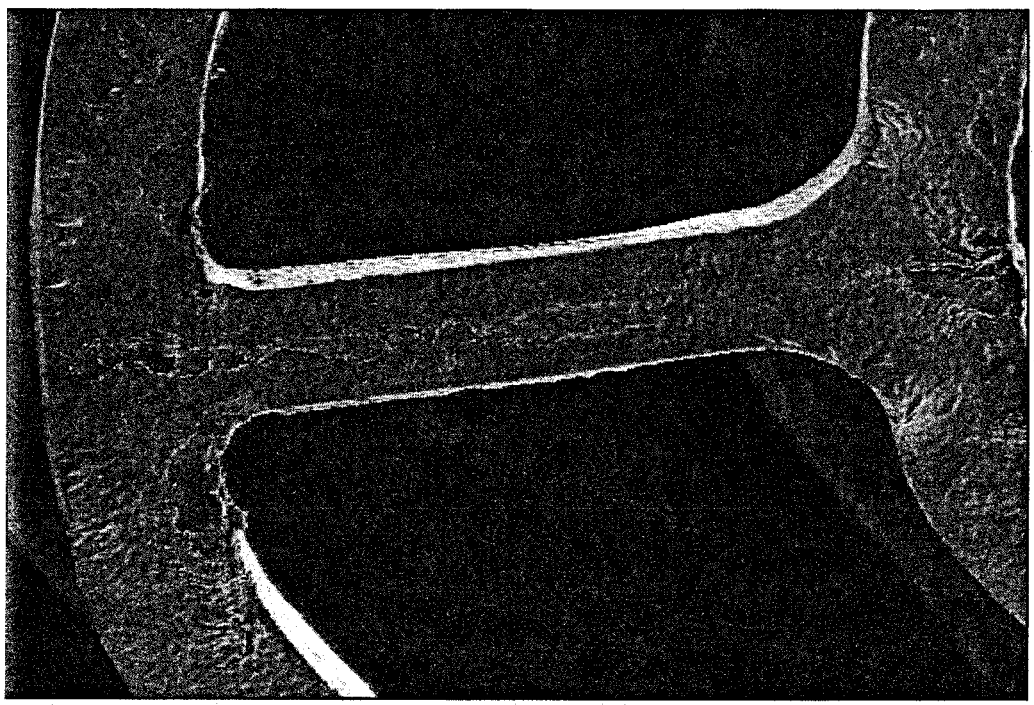
Figure 2E:
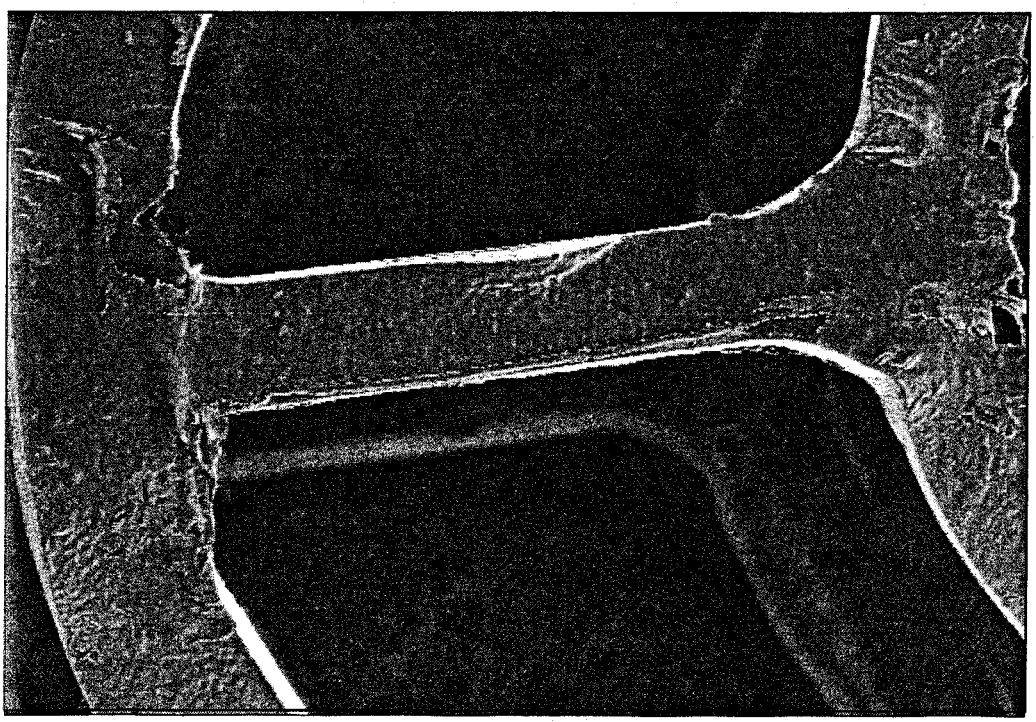

The foregoing problems caused by shear stresses induced in the coating can be exacerbated when a polymer sheet material is disposed within the aperture of the crimper jaws, between the blades and scaffold. The polymer material is provided to protect the surface of the scaffold (the backbone, or load-bearing struts, the coating or both) from indentations and other damaging effects caused by the crimping blades, which have a much higher surface hardness than the scaffold polymer. The polymer sheets can also be made of a non-stick material, such as PTFE, to minimize adhesion to the scaffold surfaces. But the presence of the polymer sheets may also amplify the Y-axis torque applied to the scaffold surface. This effect can be appreciated from FIG. 1B. As indicated by the rotation direction R, the sheet portions 124a, 125a under tension T1, T2 move in opposite directions from each other as the blades move. The sheets may apply additional torque on the scaffold if the tension T1 becomes different from T2 during crimping. As the blades close down on the scaffold this rotation applied by the sheets continues, in unison with the blades. The polymer sheet becomes pinched between the blades and polymer struts while the sheets continue to move in opposite directions. The surface-to-surface contact between the sheets and scaffold surface can amplify the shearing stresses. FIGS. 2A-2D are photos reproduced from Scanning Electronic Microscope (SEM) images of the abluminal surfaces of scaffolds crimped using a film-head crimper. These images show the damage caused to the coating by the film-head crimper.

In response to these problems associated with a Y-axis torque applied to scaffolds by crimper blades, there is a crimping process and apparatus that allows, or imparts a rotation to the catheter to reduce the Y-axis torque. A reduction of the torque should produce a concomitant reduction in shearing stress in the coating and less damage to the coating. Embodiments of the method and apparatus are discussed below. The embodiments apply either to crimping mechanisms that dispose a polymer sheet between the scaffold and blades, e.g., a film-head crimper, or a crimping apparatus that does not place a polymer sheet between the jaw blades and scaffold.

A. Loading Stage on Bearings (Free Rotation)

Figure 3A:
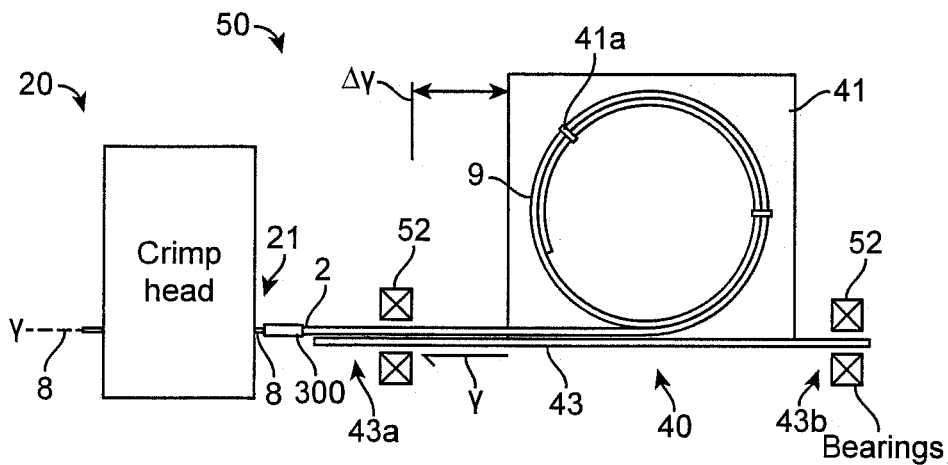
FIGS. 3A, 3B, 3C and 3D are schematic drawings describing a first, second and third embodiment of the invention, respectively.

Referring to FIG. 3A there is a shown a schematic drawing of a crimping apparatus 50. The apparatus is configured to reduce the Y-axis torque on a scaffold during crimping. Shown is the crimp head 20 having a crimp aperture 21. A catheter 9 having a catheter shaft 2 is mounted on a support frame or loading stage 40 used to guide the scaffold 300 (disposed at a distal end of the catheter 9) into, and remove the scaffold 300 from the aperture 21. The stage 40 may include a tray 41 with clips 41a to hold a proximal portion (i.e., portion nearest the catheter hub or handle) of the catheter 9 in a coiled fashion, and a channel 43 to guide the distal portion of the catheter (where scaffold 300 is located) into the aperture and align the shaft 2 with the crimp head axis (Y-axis). As indicated by "Y", the support frame or stage 40 displaces the catheter 9 and scaffold 300 along the Y-axis, to insert the scaffold 300 into, or remove the scaffold 300 from the aperture 20a. The stage 40, which includes a tray 41 and a channel 43, may have a similar design as that described in US20140189994 (as described in FIGS. 4A, 4B and 4C and accompanying description at paragraphs [0069] through [0079]), except as follows.

The setup in US20140189994 is similar to known crimping processes in that both the catheter 9 and mandrel 8 are fixed in Y-axis rotation, or can only translate in Y during the crimp process. Like the setup in the '994 application the mandrel 8 may be fixed in place but stage 40—specifically the guiding channel 43—is supported upon rotary bearings 52 at ends 43a, 43b. The rotary bearings 52 allow the stage 40 to freely rotate about the Y-axis. Hence, the catheter 9 and scaffold 300 (supported on stage 40) become decoupled from the mandrel 8 in Y-axis rotation. When the scaffold 300 is placed within the aperture 20a using stage 40 and the crimping mechanism bears down on the scaffold 300, the stage 40 rotates about the Y-axis in response to a torque applied to the scaffold 300 through blade motion. This freedom to rotate should reduce the magnitude of the shear stress in the coating during crimping. This beneficial result, provided by mounting the stage 40 upon rotary bearings 52, may be explained as follows. Using bearings 52, the torque applied to the scaffold 300 and catheter 9 induce at least a partial angular acceleration or movement in the catheter 9 distal end, which means less reactive torque (applied by the scaffold on the blades to resist rotary motion) carried by the coating in the form shear stress.

Figure 3B:
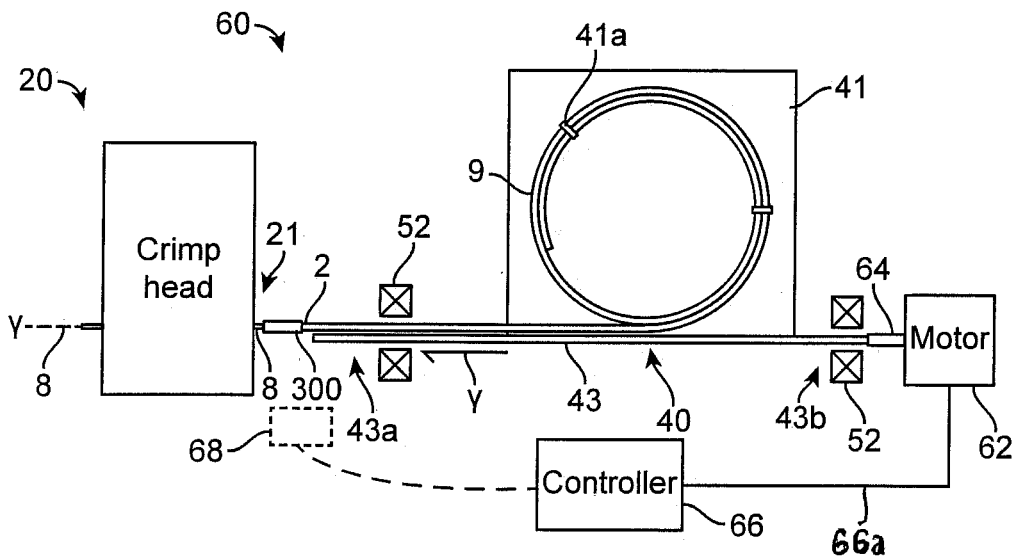
Figure 3C:
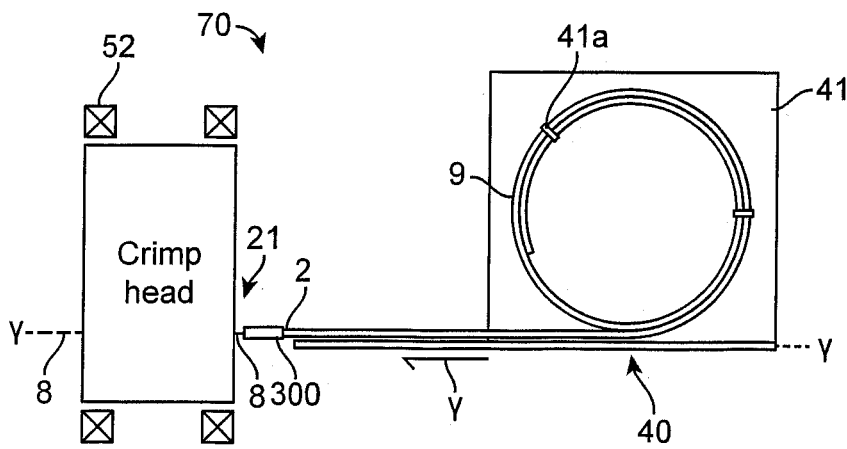
Figure 3D:
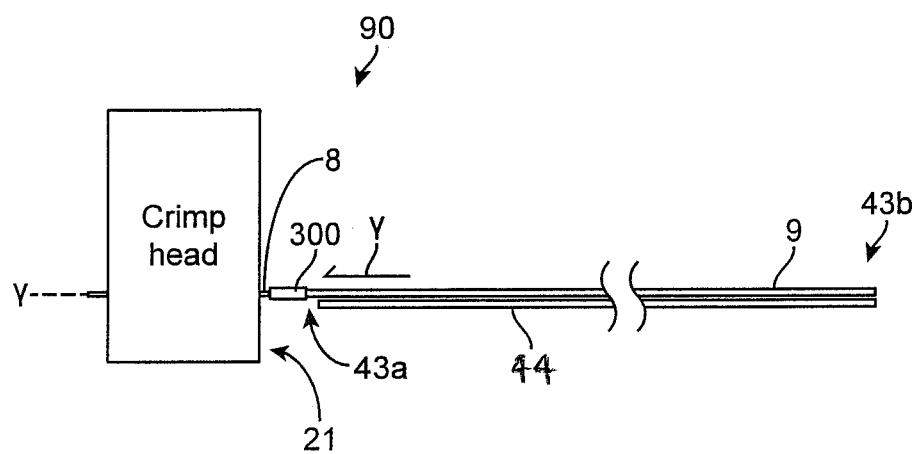

Referring to FIG. 3D, an alternative to the catheter 9 coiled and held on the tray 41 during crimping is to have the catheter 9 arranged in a straight configuration. The channel 43 and bearings 52 in FIG. 3A are replaced by a flat, frictionless surface 44. The catheter simply lays flat on this low friction surface during crimping. This arrangement enables the catheter 9 to freely rotate about the Y-axis in response to any torque applied at the distal end 43a during crimping. The embodiment illustrated in FIG. 3D, in contrast to the embodiments using a tray 41 and coiled catheter, may be preferred because free rotation of the channel 43 and catheter 9 within the bearing 52 design of FIG. 3A may be hampered by the effect of gravity acting on the coiled-catheter as it and the tray 41 rotate about the Y-axis. This effect of gravity will easily overcome any torque applied to the scaffold by the crimp mechanism. In another embodiment this influence by gravity may be overcome by modifying the tray 41 to have a counterweight or balancing inertia. The balancing inertia reduces or negates the influence of gravity-induced torque acting on the tray and coiled catheter during rotation about the Y-axis.

Referring to the above embodiment and in all other embodiments disclosed herein, a bearing may be metal or plastic. An example of a suitable bearing would be assembled by inner and outer races having ball bearings held within the races. The inner race would be formed on, or attached to the channel 43 while the outer race would be held within a housing that is mounted on the table top adjacent the crimp head (e.g., as shown in FIG. 4B). Alternatively, the bearing may be a frictionless, annular collar that receives the channel. The collar would allow the channel 43 to translate or rotate within the collar. Or the inner surface of the collar may include a groove to receive a matching rib formed on the channel so that the collar permits rotation about Y-axis, but not translation along the Y-axis relative to the stage or channel 43. Magnetic bearings or air bearings are also possible.

For the embodiments illustrated in FIGS. 3A-3C the catheter is held on the tray 41 in a coiled manner. As mentioned above, the mandrel 8 is situated within the guidewire lumen and moves with the catheter. Given that the catheter 9 may rotate about Y-axis and the proximal portion is coiled (as shown) the mandrel preferably does not pass through any of the proximal portion. Thus, a mandrel 8 may have a shortened length so that it does not extend into the coiled portion of the catheter 9, or the catheter shaft 2 portion not coiled may be lengthened. For example, the mandrel may end or protrude from a notch located near the distal end to the left of the coiled portion of the catheter 9 in FIG. 3A (e.g., a notch exit opening for a guidewire found in Rapid Exchange or RX catheters). Although not shown, the proximal end of the catheter may also have an inflation lumen for the balloon, connected to a pressurized fluid source for inflating the balloon during crimping. As with the mandrel 8 the attached pressure source is connected in such a manner to avoid any similar resistance to Y-axis rotation. This attribute of the attached pressure source also applies to the embodiment in FIG. 3B.

B. Motor—Rotation Assistance Using Motor

Referring to FIG. 3B, there is a shown a schematic drawing of a crimping apparatus 60. This embodiment is the same as apparatus 50 shown in FIG. 3A, except that apparatus 60 additionally includes a motor 62 and controller 66 for providing an assisting torque on the catheter shaft 2 to urge it to rotate in the direction of the crimp head, i.e., the rotation direction of the blades. The controller sends a command signal to motor 62 via communication link 66a.

It may be desirable, in order to further reduce shear stress in the coating, to actively rotate the catheter in the direction of the blade rotation. Although resting on bearings 52, frictional resistance in the Y-axis rotational direction, torsional flexibility in the catheter shaft 2, or a combination of the two may nevertheless produce at the distal end of the catheter 2 a resistance to rotation, which produces the undesired Y-axis torque on the scaffold (even when using bearings 52). By providing an assisting torque for the stage 40 via motor 62 this torque may be further reduced, thereby further minimizing damage to the coating.

According to one embodiment, the motor 62 that provides the torque (or enforced rotational displacement) may be a three-phase DC brushless motor connected to stage 40 at the end furthest from the crimp head 20. The rotor of the motor 62 is connected to the stage end 43b via a coupling 64, as shown in FIG. 3B. The motor may be coupled to stage 40 at end 43b (as shown), or it may be positioned to apply a rotational displacement to the stage 40 just to the left of the tray 41 in FIG. 3B. The motor 62 is energized by, or receives command signals from a controller 66. These command signals, which cause the rotor to turn at designated times during crimping and by a designated amount (e.g., 2 degrees over 10 seconds), may be derived in whole or in part from the programmed crimping sequence used to crimp scaffold 300 (an example of a programmed crimping sequence is illustrated in FIGS. 5A-5B). This programmed crimping sequence specifies the times when the aperture is closed to compress the scaffold diameter, the percentage diameter reduction occurring at those times and the rate at which the aperture is closed down on the scaffold. This information, combined with the corresponding arc-length of rotation in the catheter shaft 2 (either directly by measuring it, or estimating it from the rotation of the blades), may be used to derive the command signal for controller 66 to match an enforced rotational displacement at the end 43b of the stage 40 using the motor 62 rotor to the rotational displacement of the catheter shaft 2 proximal the scaffold and balloon.

The amount of rotational displacement applied to the end 43b of stage 40 by the motor 62 between each crimping stage (FIG. 5B) may be determined from previous measurements of a catheter shaft 2 rotation during crimping. The rotational displacement of the scaffold within the crimp aperture, when allowed to freely rotate within the crimp aperture, may be measured in the following way. A test scaffold is mounted on a shortened catheter (i.e., cut-off shaft portion of balloon catheter to leave only portion nearest balloon section at distal end, with proximal portion of remaining catheter shaft protruding out from crimp aperture). A marker may be placed on this end of the catheter shaft (or pin placed through the shaft). The start position of the marker or pin is noted. The scaffold is then subjected to the same crimping sequence used for crimping scaffolds balloon catheters (e.g., the sequence in FIGS. 5A-5B having aperture reductions sequences between crimping stages). The aperture is brought down on the scaffold and balloon in the manner it would between each crimping stage. For each diameter reduction during crimping stages, the amount of rotation in the scaffold and catheter shaft is measured, by comparing start and end points of the pin or marker. Now, for each period between stages, divide the measured angle (or arc-length) by the rate at which the aperture diameter is being reduced (available from crimp recipe) to arrive at a rotation rate for the motor 62. Using this information, the controller 66 command signal may be derived for the crimping sequence, synchronized with the times and duration of the respective diameter reductions of the scaffold. Thus, in reference to FIGS. 5A-5B, the controller 66 command signal causes the motor 62 rotor to rotate at the rate and duration corresponding to the previously measured rotations of the catheter shaft between each of the respective crimping stages, as shown below in TABLE 1.

TABLE 1

Examples of rotation applied to stage 40 of FIG. 3B by motor 62 based on measured rotations of catheter shaft when scaffold on inflated balloon (ambient to 200 psi with pressurization dwells from 1 to 10 seconds) compressed in crimp head using process flow in FIGS. 5A-5B (n = 3)

| Step | Crimping Sequence programmed for crimper | Command Signal Sent to Motor 62 by Controller 64 | General Mode of Action |
|---|---|---|---|
| Stage I | Reduce jaw aperture in size by 46% in 2 seconds Balloon pressurized to 100 psi ± 5 psi | No rotation needed | Scaffold does not rotate, jaw blades begin closing at 0.25" to 0.136" at 0.1 in/s, dwell 15 seconds |
| Stage II | Reduce jaw aperture in size by 6% in 3 seconds Balloon pressurized to 50 psi ± 5 psi | Rotate catheter and stage | Scaffold rotates, blades close from 0.136" to 0.128" at 0.003 in/s, angular rotation of about 2 degrees, dwell 10 seconds |

TABLE 1-continued

Examples of rotation applied to stage 40 of FIG. 3B by motor 62
based on measured rotations of catheter shaft when scaffold on inflated
balloon (ambient to 200 psi with pressurization dwells from 1 to 10 seconds)
compressed in crimp head using process flow in FIGS. 5A-5B (n = 3)

| Step | Crimping Sequence programmed for crimper | Command Signal Sent to Motor 62 by Controller 64 | General Mode of Action |
|---|---|---|---|
| Stage III | Reduce jaw aperture in size 30% in 1 second Ambient pressure | Rotate catheter and stage | Scaffold rotates, blades close from 0.128" to 0.09" at 0.003 in/s, angular rotation of about 10 degrees, dwell 5 seconds |
| Stage IV | Reduce jaw aperture in size by 11% in 4 seconds Ambient pressure | Rotate catheter and stage | Blades close from 0.09" to 0.08" at 0.003 in/s, angular rotation of 1 degree, dwell 10 seconds |
| Stage V | Increase jaw aperture in size by 5*% in 1 second Balloon pressurized to 200 psi ± 5 psi | No rotation needed | Blades open from 0.1" to 0.105" at 0.05 in/s, dwell 10 seconds |
| Stage VI | Reduce jaw aperture reduces in size by 33% in 12 seconds Balloon pressurized to 200 psi ± 5 psi | Rotate catheter and stage | Scaffold rotates, blades close from 0.105" to 0.070" at 0.05 in/s measured shaft angular rotation of about 10 degrees, dwell 8 seconds |
| Stage VII | Increase jaw aperture reduces in size by 7% in 1 second Balloon pressurized to 200 psi ± 5 psi | No rotation needed | Blades close from 0.070" to 0.075" at 0.003 in/s, dwell 10 seconds |
| Stage VIII | Reduce jaw aperture reduces in size by 40% in 10 seconds Balloon pressurized to 200 psi ± 5 psi | Rotate catheter and stage | Scaffold rotates, blades close from 0.075" to 0.0450" at 0.005 in/s angular rotation of about 5 degrees, dwell 10 seconds |
| Stage IX | Increase jaw aperture reduces in size by 11% in 1 second Balloon pressurized to 200 psi ± 5 psi | No rotation needed | Blades close from 0.045" to 0.050" at 0.005 in/s angular rotation of less than 1 degree, dwell 5 seconds |
| Stage X | Reduce jaw aperture reduces in size by 28% in 5 seconds Balloon pressurized to 200 psi ± 5 psi | No rotation needed | Blades open from 0.050" to 0.036" at 0.003 in/s angular rotation of less than 1 degree, dwell 5 seconds |

Alternative to these measurements, the rotation amount may be derived based on a fixed relationship between rotational movement of the blades and diameter reduction in the aperture. For an iris or sliding-edge crimping, there exists a fixed relationship between change in aperture size and rotation of the crimp blades. Given this, it may be reasonable to assume that a rotation amount of the blades during each diameter reduction will be about the same as the targeted amount of rotation of the catheter shaft. Accordingly, the rotation amount and rate of the blades during each diameter reduction in FIGS. 5A-5B may be directly input to the controller for rotating that motor rotor by the same amount as the blades.

C. Motor Rotation as Function of Number of Blades and Blade Movement

The sliding or rotating wedge crimper is extensively used to crimp stents and bioresorbable scaffolds. The angle at the tip of the wedges is determined by the number of wedges. When the crimper is fully closed, the tips of the wedges fit together perfectly and completely close off the aperture. Hence, the tip angle of the wedges may be calculated using:

$$\text{Wedge tip angle} = \frac{360}{\text{Number of wedges}}$$

Hence, for 12 wedges, the tip angle is 360/12 = 30 degrees.

When the crimper is not fully closed, and the wedges are in contact, they fit together to form an aperture with a polygonal shape. The number of sides of the polygon is equal to the number of wedges. This polygon becomes uniformly smaller as the crimper is closed. Consequently, the sides of the polygon become uniformly shorter as the crimper is closed.

The wedges translate and rotate inwards to close the aperture. The crimper wedge movement can be one of pure translation. However, the wedges can also rotate but they must also translate for the aperture to close. It is the case that pure rotation of the wedges is not sufficient to close the aperture.

Focusing on the sides of the polygon formed by the wedges, a circular object being crimped makes contact with the side of the polygons at the midpoint of each side. Understanding how this contact point, lying in the middle of each side of the polygon, moves as the crimper is closed is important to understanding the rotation that is imposed upon the object during crimping. In order to study a simple case, we will first consider a crimper with just three wedges as depicted in FIG. 8A.

Figure 8A:
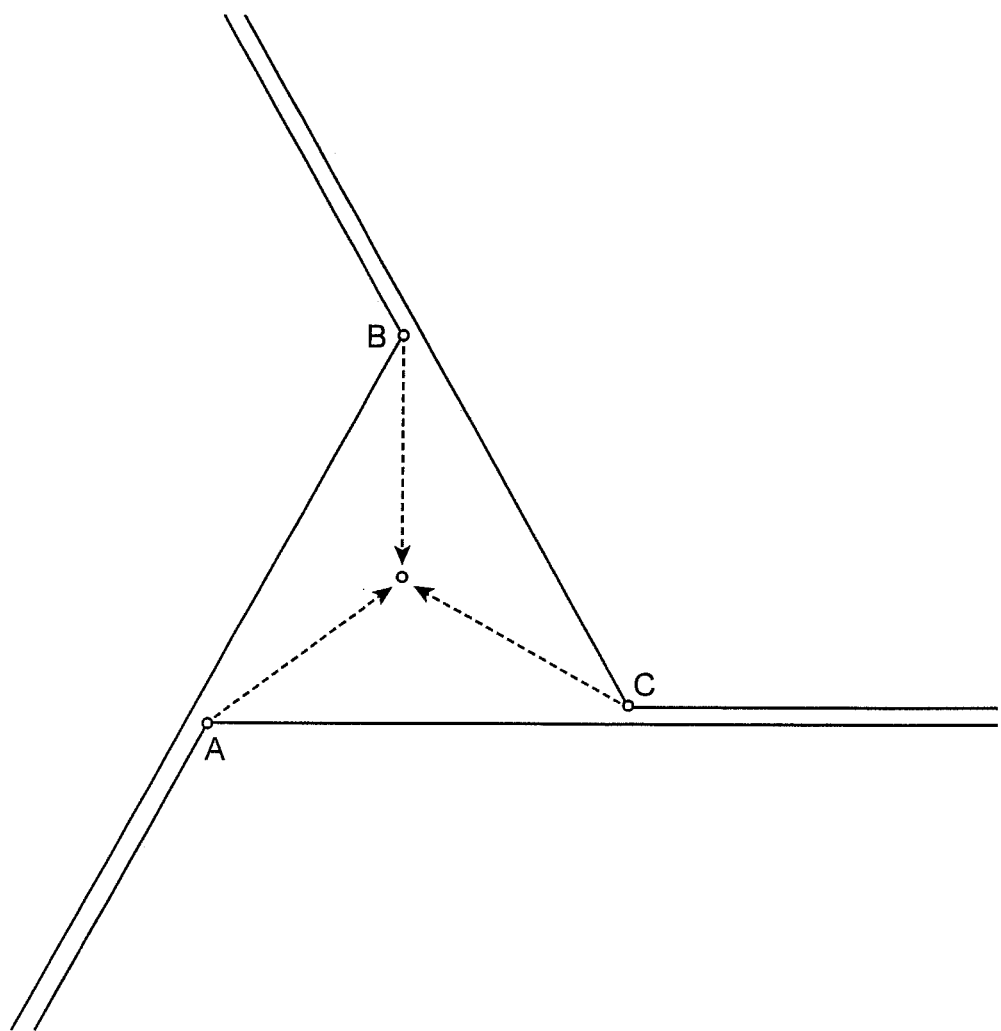
FIG. 8A is a first schematic diagram showing an aperture of a three-wedge crimper. This figure illustrates exposed wedges and direction of travel of points A, B, C as the wedge faces converge upon the aperture axis.

In FIG. 8A, the wedge movement can be visualized by imaging the points labeled as A, B, and C moving along the dotted lines towards the center of the aperture. The face of each wedge forming the aperture maintains its relative orientation as the wedges translate. A stent in the aperture has its diameter reduced as the wedges move inwards. What is more subtle is that, in this case, the stent will rotate counter clockwise as the aperture is closed. If the wedges are each flipped about an axis perpendicular to their exposed faces, the aperture closes in the same way but an inserted stent will rotate clockwise as the aperture is closed.

A stent will only be rotated during crimping when it is in contact with all the wedges. Calculating the amount of rotation first requires relating the aperture opening to the size of an inscribed circle. This can be done with the aid of FIG. 8B.

Figure 8B:
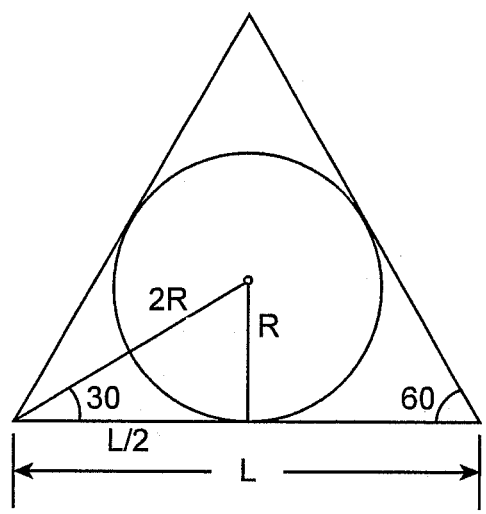
FIG. 8B is a second schematic relating circle dimensions to dimensions of the wedges from FIG. 8A.

From FIG. 8B, we can get the geometric relation:

$$L = 2\sqrt{3}R \quad (1)$$

and $$\frac{dL}{dR} = 2\sqrt{3} \quad (2)$$

Figure 8C:
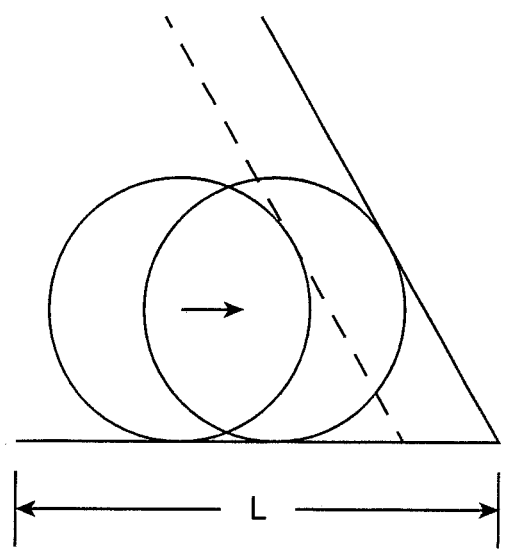
FIG. 8C is a third schematic drawing relating to FIGS. 8A and 8B.

Next, a relation is needed for how the stent is rotated as a function of changes in the length of L, the length of the exposed wedge face. FIG. 8C depicts this rotation and is useful for visualization. In FIG. 8C, the depiction is of the aperture opening which is the same process in reverse as the aperture closing. L changes by length ΔL. The center of the circle also translates to the right by ΔL. A 360 degree rotation of the circle moves its center by 2πR. From FIG. 8C, the instantaneous relation between changes in side length L and the degree of rotation is Equation 3.

$$D = \frac{360}{2\pi R} \Delta L \quad (3)$$

Where D is the rotation in degrees and ΔL is the change in side length. Rearranging this relation we have:

$$dL = \frac{2\pi R}{360} dD \quad (4)$$

Equations 2 and 4 can be combined and integrated to give:

$$D = \frac{\sqrt{3}(360)}{\pi} \ln\left(\frac{R_2}{R_1}\right) \quad (5)$$

Figure 8D:
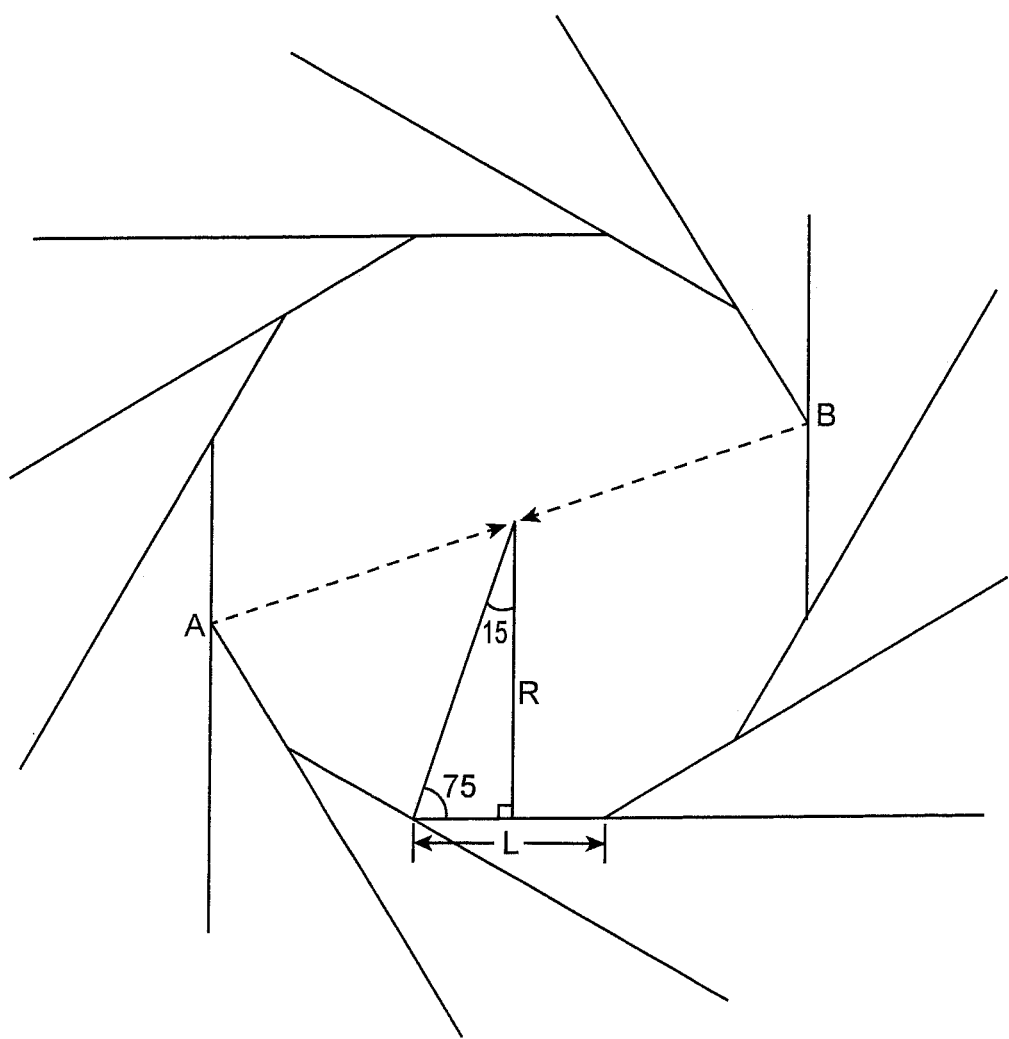
FIG. 8D is a schematic showing a twelve-wedge crimper.

Equation 5 gives the rotation in degrees in going from a radius $R_1$ to $R_2$ and vice versa. For example, for a bioresorbable scaffold where the radius is brought from 1.75 mm (3.5 mm OD) to 0.75 mm (1.5 mm OD), the rotation is 168.2 degrees for a crimper with just three wedges. Commercial sliding wedge crimpers for stents and scaffolds have many more than just three wedges. A common number of wedges is twelve. A larger number of wedges has the advantages of:
   Forming a more circular aperture
   Distributing the crimping forces in a more circumferentially uniform manner
   Less imparted rotation imparted to the stent or scaffold during crimping FIG. 8D is a drawing of a twelve wedge crimper.

In this mechanism, the points A and B, representing the tips of two wedges, move inwards as shown by the dotted lines. In the limit of an infinite number of wedges, the amount of rotation imparted to a stent/scaffold during crimping would be zero for a crimper where the edges move by translation. Equation 6 shows how L changes with the inscribed circle radius for a twelve wedge crimper.

$$L = \frac{2R}{2 + \sqrt{3}} \quad (6)$$

The derivative of equation 6 can be combined with Equation 4 to give the rotation as a function of change in radius R.

$$D = \frac{360}{\pi(2 + \sqrt{3})} \ln\left(\frac{R_2}{R_1}\right) \quad (7)$$

Using Equations 5 and 7, the amount of rotation can be compared between a three wedge and a twelve wedge crimper when going from a 3.5 mm OD to a 1.5 mm OD.

| Number of Wedges | Degree of Scaffold Rotation in Going from 3.5 to 1.5 mm OD |
| --- | --- |
| 3 | 168.2 |
| 12 | 26.0 |

As one would predict, the larger number of wedges decreased the amount of rotation. However, even with twelve wedges, the degree of rotation is measurable.

D. Motor—Closed-Loop System

According to one embodiment a stepper motor may be used for motor 62. This type of motor is capable of applying very accurate rotational displacements to the stage 40. The stepper motor 62 may be operated in open loop fashion as described above in connection with FIG. 3B, or in a closed loop fashion, i.e., command signal adjusted or derived from feedback. A torque sensor (not illustrated) measuring the relative torque between the jaws and the catheter may be used for feedback. The rotor of the stepper motor is coupled to the stage 40 channel 43 via coupling 64, as before. As the relative torque increases, the stepper motor would use the feedback to rotate in the direction (or at a higher or lower speed) to reduce the relative torque.

The relative torque is directly relatable to whether the motor rotor is turning the catheter in synch with the rotating blades/catheter distal end, driving the catheter faster than the blades, or lagging the turning blades, respectively. If there is no relative torque, then this may indicate the catheter shaft at the motor-rotor coupling 64 is turning at the same rate as the scaffold/distal end, i.e., no shear stress across coating thickness (assuming catheter shaft is rigid in torsion).

E. Crimp Head Counter-Rotates

Referring to FIG. 3C, in still another embodiment the crimp head may be supported on bearings 52 to enable it to rotate about the Y-axis, rather than the catheter 9, or the crimp-head may include a counter-rotation mechanism to the rotation of the blades. In this embodiment the catheter is fixed in Y-axis rotation. As the crimp aperture closes down on the scaffold 300, the generated torque causes the crimp head to rotate about the Y-axis (since it rests on bearings 52), rather than the scaffold or catheter. As a consequence, there should be less torque applied to the scaffold. The rotation of the crimp head would be opposite to the direction of torque applied to the scaffold, thereby resulting in no net torque on the scaffold. The net-zero torque may alternatively be implemented by a counter-rotation mechanism external to the crimp head that counter-rotates the crimp head in proportion to the incremental angular distance that the blades travel through when the aperture changes size. This counter rotation may be stepper motor controlled and implemented with a pre-programmed amount of motion corresponding to the blade movement occurring during a crimp process (see e.g. infra discussion, FIGS. 5A-5B). In this way, the net-torque applied to the scaffold and catheter may be reduced.

Figure 4A:
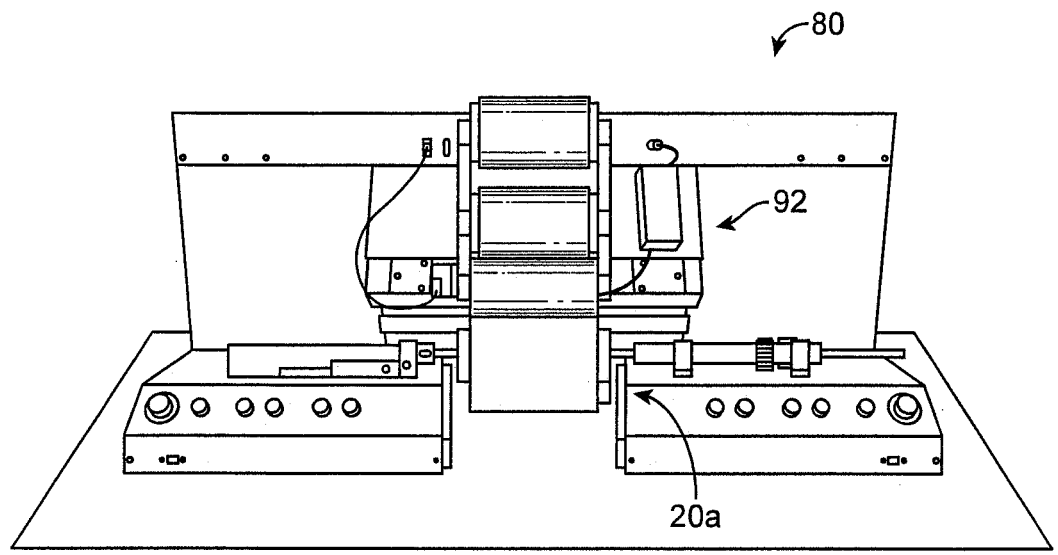
FIGS. 4A and 4B are two perspective shows of a crimping apparatus according to a fourth embodiment of the disclosure.
Figure 4B:
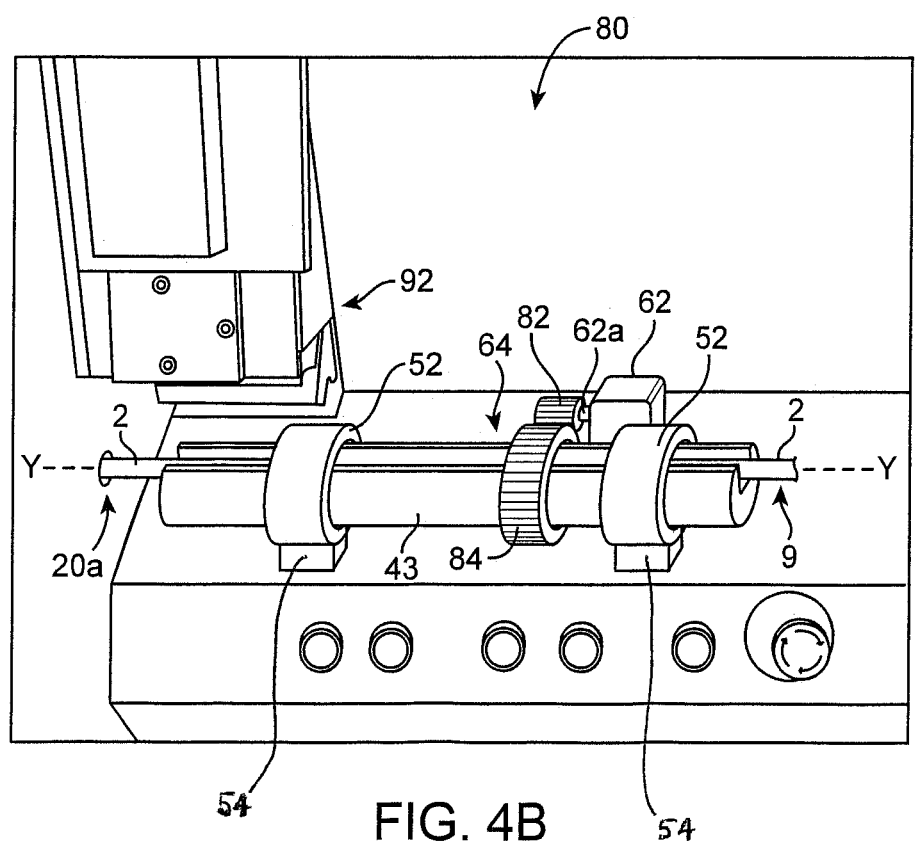

Referring to FIGS. 4A, 4B there is shown two views of a second embodiment of a crimping apparatus 80. These figures show partial views of a crimping station similar to that depicted in the '994 application. As shown the channel 43 has a groove to receive, hold or maintain the catheter shaft 2 in alignment with the Y-axis (e.g., using magnets). Catheter with shaft 2 may also be threaded into groove from the distal end with the catheter shaft secured into channel 43 by a clamping mechanism. The channel is supported by bearings 52 (the channel 43 may include, or be connected to the inner race of the bearing 52, as explained earlier, or the bearing may be a frictionless collar with a groove receiving a matching circular rib formed on the channel 43 to permit only rotation about Y-axis). A housing of the bearing 52 includes posts or legs 54 that may be coupled to a translation mechanism (not shown) for moving the channel 43 towards or away from the aperture 20a opening.

The motor rotor 62a rotation/torque is communicated to the channel 43 via the coupling 64, which in this case includes a first gear 82 intermeshed with a second gear 84 for transferring the motor torque to the channel 43 and, thereby, to the catheter 9. The gear ratios of the first gear 82 to the second gear 84 may range from 20:1 to 30:1. The second gear is fixed to the channel 43 and the motor rotor 62a rotates about an axis parallel to the Y-axis. The proximal end of the shaft 2 of the catheter 9 may be straightened out fully, or coiled up and stacked on a tray as before. The motor 62 may be a stepper motor controlled by the controller 66 and operated in open loop or closed loop fashion, as explained earlier.

The crimping station includes a vision system 92 (similar to the vision system and associated image detection system described in the '994 application). The system 92 may be used to measure the rotations of the catheter shaft, in the event the motor command signal is based on measured rotations of the shaft between crimping stages. For example, the shaft may be marked with a substance illuminated in ultraviolet light, then movement of this mark tracked by the camera between crimping stages to determine the amount of rotation in the shaft.

FIGS. 5A, 5B are flow diagrams illustrating an example of a crimping process that may incorporate embodiments discussed in connection with FIGS. 3A-3C, and 4A-4B. In the example the scaffold crimped to the balloon is laser cut from a radially expanded tube. However, the crimping process is not limited to a scaffold made from a laser-cut polymer tube. Other scaffold types, e.g. a scaffold not radially expanded, scaffolds formed by braiding, injection molding, casting or scaffolds fabricated from an extruded polymer sheet (as opposed to a tube) are within the scope of disclosure. Additionally, the starting outer diameter sizes for the stent or scaffold may be from 2.5 mm to 4.5 mm, for a coronary stent or scaffold. The crimping process described may also be used for a peripheral stent or scaffold having outer diameter sizes of between 5.0 mm and 10 mm.

The crimping process may use one or two balloons. The two balloons referred to in the figures, and discussion below, are called "Balloon A" and "Balloon B." The Balloon A refers to the balloon of the balloon catheter of the finished product. The Balloon B refers to a temporary or sacrificial balloon, or balloon catheter that is used during the initial crimp stages then replaced by the Balloon A at the time of a final alignment check, as explained below. Practice of the crimping process using Balloon B (later replaced by Balloon A) is desirable when the starting inner diameter size of the scaffold is larger than, or the same size as the diameter of the Balloon A when Balloon A is inflated to its nominal inflation diameter, or when Balloon A is inflated beyond this size.

In a preferred embodiment of a crimping process a film-head crimper is used to crimp the scaffold to the balloon catheter. For a film-head crimper, the polymer material in the form polymer sheets dispensed from a pair of rolls (FIGS. 1A-1B) is used to protect the scaffold from the blades of the crimper. It will be understood, however, that the invention is not limited to using a film-head crimper, or crimper that inserts polymer material between crimper blades and the scaffold.

Referring to FIGS. 5A-5B, in this example two crimper settings or setups are used. The first crimper setup is used for the crimping stages that precede a final alignment check (FIG. 5A) and the second crimper setup is used for the stages that follow the final alignment check (FIG. 5B). In other examples one crimping station may be used for all stages. A summary of the crimp process is described now.

Pre-Crimp Procedure:

The scaffold is placed on Balloon A (or Balloon B if two balloons will be used). The balloon is inflated to its nominal diameter or post-dilation diameter (greater than nominal diameter size) or, more generally, the balloon is fully inflated so that its size is at least equal to or exceeds the inner diameter of the scaffold in order to support the scaffold during the initial crimping steps. The scaffold is aligned with proximal and distal markers on the balloon (not necessary if Balloon B is used). The crimper head, scaffold and/or balloon may also be deionized to remove static charge buildup that can cause the scaffold to shift out of alignment with balloon markers during crimping. Static charge buildup has been found to not only cause misalignment between the scaffold and balloon, but also cause irregular crimping of the scaffold (stents typically do not have to worry about static charge buildup because the balloon is in sliding contact with a metal, as opposed to a polymer surface). The scaffold is then inserted into the crimper head while the balloon remains fully inflated.

Stage I:

The scaffold supported on the fully inflated balloon is within the crimp head. The temperature of the crimp-head or crimping temperature is set during this stage, as is the starting iris or aperture size corresponding to the input outer diameter of the scaffold (e.g. 3.5 mm). In a preferred embodiment blades of an iris or sliding wedge crimping device are heated to achieve the desired crimping temperature (alternatively a heated fluid such as air or nitrogen may be used). After the scaffold reaches the crimping temperature, the iris of the crimper closes to reduce the scaffold inner diameter (ID) to less than the outer diameter (OD) of the fully inflated balloon and while the balloon remains fully inflated. For the preferred embodiments employing a motor to apply a rotation, no rotation is applied during the Stage I diameter reduction. However, it is contemplated that rotation may be desired at any stage during a crimp process.

Stage II Through IV:

The crimper jaws are held at a fixed diameter for a dwell period and while the balloon is fully inflated. At the conclusion of this dwell period the scaffold and fully inflated balloon are removed from the crimping device.

Verify Alignment/Replace Balloon:

Removal after Stage II may be skipped if there is no need to check or verify final alignment with balloon markers, or if Balloon A is used for Stages I and IX. In the illustrated embodiment the scaffold supported on the fully inflated balloon is removed from the crimping device to verify that the balloon is located between the balloon markers (when Balloon A used for Stages I and V), or Balloon B is replaced with Balloon A and the scaffold aligned with the balloon markers.

Referring now to FIG. 5B, Process I continues. In the following discussion, and as indicated in FIG. 5B, there is a re-set of the polymer material indicated. This is an optional step and may be removed or eliminated. The re-set step is not necessary to practice the invention, but may be included to help relieve any torque that might have built up on the scaffold after successive diameter reductions. The re-set may also be desired to remove any excess polymer material that builds up between the crimp blades and scaffold as the scaffold diameter is reduced in size. Excess polymer material between the blades and scaffold can interfere with the rotation of scaffold struts about crowns (or crests), thereby potentially affecting the structural integrity of the backbone or uniformity of expansion of the scaffold form the crimped state.

Stage V:

After the scaffold and fully inflated Balloon A are returned to the crimper, the iris diameter is set at a slightly higher diameter than the scaffold diameter at the conclusion of Stage IV (to account for recoil). The iris or aperture size is held constant for a time period sufficient to bring scaffold temperature back to crimping temperature.

After the crimping temperature is reached, the scaffold diameter is reduced down while the balloon is pressurized. The balloon is preferably fully inflated for the diameter reduction following Stage V. For embodiments employing a motor to apply a rotation to the channel 43 or catheter shaft 2, a rotational amount derived from any of the methods discussed earlier (i.e., empirical, formula or using feedback loop) may be applied during the Stage I-IV diameter reduction.

Stage VI-IX:

The crimp aperture is held constant for a dwell period after scaffold diameter is reduced from the Stage V diameter. The polymer sheets of the film headed crimper may be re-set to remove excess sheet material from within the aperture when the scaffold diameter was reduced.

These stages follow a similar process as in Stages III-IV: perform a dwell at each of the stages with a diameter reduction between the stages, and apply a rotation to the channel 43 or catheter shaft 2 according to any of disclosed methods (assuming a motor is used). In total, there may be 2, 3, or between 2-5 times where the motor (if used) rotates the channel 43 and/or catheter shaft 2 during a diameter reduction. The rotations all occur following the final alignment check.

Final Crimp (Stage X)/Optional Stages:

Following the re-set (immediately after Stage VIII) there may be a number of additional, optional stages. At the conclusion of these stages there is a final pressurization of the balloon at the final crimp diameter. The pressurization may be a leak check. After this final step the scaffold is fully crimped to the balloon catheter, removed from the crimp head and placed within a constraining sheath.

Scaffold and Catheter

Figure 7:
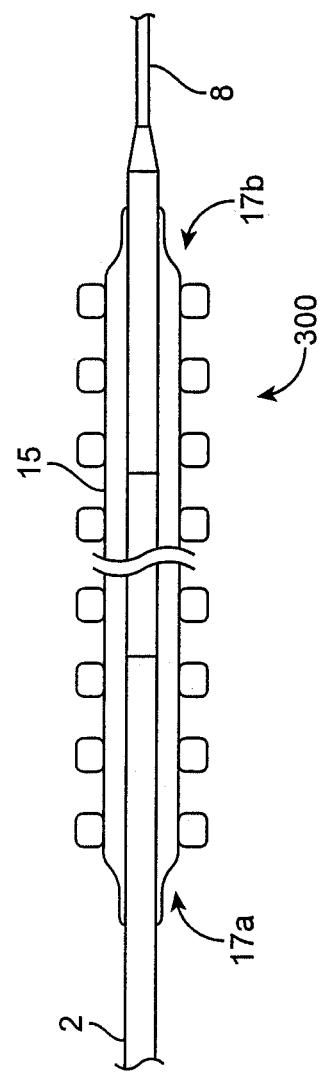
FIG. 7 shows the scaffold of FIG. 6 crimped to a balloon of a balloon catheter.

FIG. 7 illustrates a side-view of a scaffold 300 crimped to a balloon catheter, which has a shaft 2, balloon 15 with distal and proximal ends 17a, 17b (where balloon markers are found). The catheter is supported on a mandrel 8.

Figure 6:
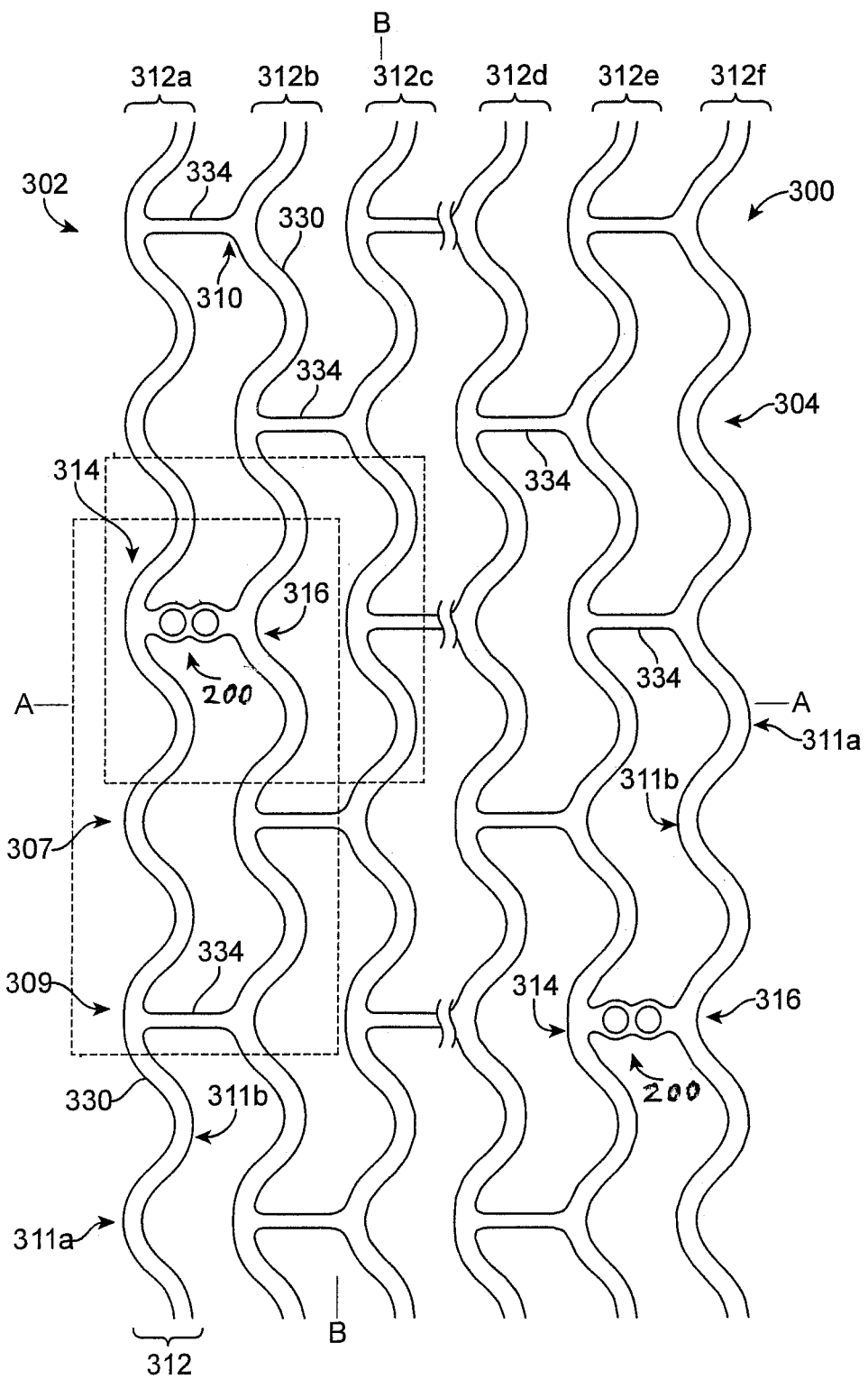
FIG. 6 shows distal and proximal end portions of a scaffold according to one embodiment.

FIG. 6 shows a partial, planer view of end portions of the scaffold 300 from FIG. 7 in an expanded or before-crimping state. This figure illustrates an example of a network of struts and links for the scaffold 300. The left or distal end portion 302 (i.e. the left side of FIG. 6) includes sinusoidal rings 312a, 312b, and 312c where ring 312a is the outermost ring. Ring 312a and ring 312b are adjoined by two links 334 and a marker link 200. Ring 312c and ring 312d are adjoined by three links 334 that extend parallel to axis A-A. The links 334 extend parallel to axis A-A and have a constant cross-sectional moment of inertia across its length, meaning link 334 has a constant width and thickness and the location of the centroid or geometric center (or longitudinal axis) of the link is everywhere parallel with axis A-A. The right or proximal end portion 304 (i.e. the right side of FIG. 6) includes sinusoidal rings 312d, 312e, and 312f where ring 312f is the outermost ring. Ring 312d and ring 312e are adjoined by three links 334. Ring 312e and ring 312f are adjoined by two links 334 and the marker link 200. Thus, scaffold 300 has a marker link 200 extending between and adjoining the outermost ring with the adjacent, inner ring. The scaffold 300 may have 15, 18 or 20 rings 312 interconnected to each other by links 334.

When reference is made to a direction perpendicular to, or parallel with/to axis A-A in FIG. 6, it will mean perpendicular to, or parallel with/to the axial direction of a scaffold or tube. Similarly, When reference is made to a direction perpendicular to, or parallel with/to axis B-B in FIG. 6, it will mean perpendicular to, or parallel with/to the circumferential direction of the scaffold or tube. Thus, a sinusoidal ring of a scaffold extends parallel with/to (in periodic fashion) the circumferential direction or parallel to axis B-B, and perpendicular to axis A-A whereas a link in one embodiment extends parallel to the axial direction or axis A-A of the scaffold or tube and perpendicular to the axis B-B. The dimension of thickness (e.g., wall, strut, ring or link thickness) refers to a dimension measured perpendicular to both of axes A-A and B-B. The dimension of width is measured in the plane of axes A-A and B-B; more specifically, the width is the cross-sectional width from one side to another side of a contiguous structure; thus, link 334 has a constant width over its length. Moreover, it is understood that the so-called plane of axes A-A and B-B is technically not a plane since it describes surfaces of a tubular structure having central lumen axis parallel with axis A-A. Axis B-B therefore may alternatively be thought of as the angular component if the scaffold locations were being described using a cylindrical coordinate system (i.e., axis A-A same as Z axis in cylindrical coordinates and location of a luminal/abluminal surface of a crown, link, ring, etc. is found by the angular coordinate and radial coordinate constant, in addition to Z).

A ring 312, e.g., ring 312b, is sinusoidal meaning the curvature of the ring along axis B-B is best described by a sine wave where the wavelength of the sine wave is equal to the distance between adjacent crests 311a of the ring. The ring has a constant width at both crowns 307, 309 and 310 and struts 330, which connect a crown to an adjacent crown.

There are three crown types present in each inner ring 312b through 312e: U-crown, Y-crown and W-crown. Outermost rings have only the Y-crown or W-crown type, and the U-crown type. A crest or peak 311a (or trough or valley 311b) may correspond to a U-crown, Y-crown or W-crown. For the outermost ring 312a there is only a U-crown and W-crown type. For the outermost ring 312f there is only a U-crown and Y-crown type. A marker link 200 adjoins rings by forming a W-crown with the first ring (e.g., ring 312e) and a Y-crown with the second ring (e.g. ring 312f).

A link 334 connects to ring 312f at a Y-crown 310. A "Y-crown" refers to a crown where the angle extending between a strut 330 of a ring 312 and the link 334 is an obtuse angle (greater than 90 degrees). A link 334 connects to ring 312a at a W-crown 309. A "W-crown" refers to a crown where the angle extending between the strut 330 and the link 334 is an acute angle (less than 90 degrees). A U-crown 307 is a crown that does not have a link connected to it. Marker link 200 connects to a ring at a W-crown 314 and a Y-crown 316.

For the scaffold 300 there are 6 crests or peaks 311a and 6 troughs or valleys 311b for each ring 312. A crest 311a is always followed by a valley 311b. Ring 312b has 12 crowns: 3 are W-crowns 309, 3 are Y-crowns 310 and 6 are U-crowns 307.

A crimped diameter enforced on scaffold 300 (using, e.g., Process I or Process II) may be expressed in terms of a theoretical minimum crimped diameter where struts that converge at the same crown are in contact with each other when the scaffold is fully crimped, i.e., when the scaffold is removed from the crimping device, or when placed within a restraining sheath soon after crimping. The equation for the theoretical minimum crimped diameter (D-min) under these conditions is shown below $$D\text{-min}=(1/\pi)\times[(n\times\text{strut\_width})+(m\times\text{link\_width})]+2*t$$

Where
"n" is the number of struts in a ring (12 struts for scaffold 300),
"strut_width" is the width of a strut measured at the luminal surface (170 microns for scaffold 300),
"m" is the number of links adjoining adjacent rings (3 for scaffold 300),
"link_width" is the width of a link (127 microns for scaffold 300), and
"t" is the wall thickness (93 microns for scaffold 300).

Hence, for scaffold 300 D-min=(1/π)×[(12×170)+(3× 127)]+2×(93)=957 microns. As can be appreciated D-min according some embodiments for crimping is not a function of a non-zero inner crown radius (as will be appreciated if the crimping did not exceed the inner crown radius then this additional sum of distances, i.e., twice the inner crown radius for each crown of a ring, would be added to D-min). Thus D-min defined above is less than a D-min where crimping does not bring struts into contact.

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in claims should not be construed to limit the invention to the specific embodiments disclosed in the specification.

What is claimed is:

1. A method, comprising:
    using a stent or scaffold, the stent or scaffold having an outer diameter and the outer diameter having a before crimping size;
    using a balloon of a balloon catheter;
    using a crimping device having a plurality of blades configured to form an aperture, wherein the blades are displaced relative to each other to increase or decrease the size of the aperture during crimping, and wherein the aperture has an axis surrounded by the blades; and
    crimping the stent or scaffold to the balloon, the crimping comprising:
        placing the stent or scaffold on the balloon,
        aligning the stent or scaffold and balloon catheter with the aperture axis, including supporting the balloon catheter using a bearing having a bearing axis parallel to the aperture axis,
        wherein when the blades of crimping device rotate about the aperture axis the aperture size changes, whereupon the catheter rotates about the bearing axis in response to the rotation of the blades about the aperture axis, and
        reducing the stent or scaffold outer diameter from the before crimping size to a first size.

2. The method of claim 1, wherein the crimping device is a film-head crimper.

3. The method of claim 1, wherein the crimping further includes the step of reducing the stent or scaffold outer diameter from the first size to a second size, and rotating the catheter about the bearing axis while the stent or scaffold outer diameter is reduced from the first size to a second size.

4. The method of claim 3, wherein the second size is at least 50% of the before crimping size.

5. The method of claim 3, wherein the catheter is rotated using a motor.

6. The method of claim 5, wherein the motor is a stepper motor.

7. The method of claim 5, wherein the motor rotates the catheter by an angle of between about 2 degrees and about 50 degrees.

8. The method of claim 5, wherein the motor rotates the catheter by no more than about 26 degrees.

9. The method of claim 3, wherein the crimping device includes polymer material disposed between the blades and the stent or scaffold during the crimping, wherein the polymer material is re-set within the aperture before or after the rotating the catheter about the bearing axis while the stent or scaffold outer diameter is reduced from the first size to the second size.

10. The method of claim 3, wherein before or after reducing the scaffold diameter from the first size to the second size the aperture is held constant.

11. The method of claim 3, wherein the catheter is rotated after the stent or scaffold diameter is reduced to 50% or less than 50% of the before crimping diameter.

12. The method of claim 1, wherein the crimping step crimps a scaffold to the balloon, and the balloon has a nominal inflation diameter, and wherein the before crimping size is greater than a nominal diameter of the balloon, the scaffold is made from a tube comprising a polymer, the polymer having a glass transition temperature, and the scaffold is subjected to a crimping temperature during the crimping.

13. An apparatus for crimping a stent or scaffold to a catheter, comprising:
- a crimp head having an opening and a plurality of blades defining an aperture and aperture axis, wherein the blades are rotated about the aperture axis to increase or decrease the size of the aperture; and
- a loading stage mounted on a surface adjacent the opening, the loading stage comprising
    - a channel aligned with the aperture axis, and
    - a bearing, having a bearing axis, that allows for rotation of the catheter about the bearing axis, and supporting the channel above the surface, wherein the bearing axis is coincident with the aperture axis.

14. The apparatus of claim 13, wherein the loading stage is coupled to a first motor for displacing the loading stage along the aperture axis, towards or away from the opening.

15. The apparatus of claim 14, wherein the loading stage is coupled to a second motor for rotating the loading stage about the bearing axis.

16. The apparatus of claim 15, wherein the second motor is a stepper motor.

17. The apparatus of claim 13, further comprising a controlled heating element to set the blades to a designated temperature.

18. A method for crimping a medical device to a balloon catheter using the apparatus of claim 13, comprising holding a balloon catheter by the loading stage during the crimping, and crimping a medical device to the balloon catheter.

19. A method, comprising:
- using a stent or scaffold, the stent or scaffold having an outer diameter and the outer diameter having a before crimping size;
- using a balloon of a balloon catheter;
- using a crimping device having an opening and a plurality of blades defining an aperture and aperture axis, wherein the blades are rotated about the aperture axis to increase or decrease the size of the aperture; and
- crimping the stent or scaffold to the balloon, the crimping comprising:
    - placing the stent or scaffold on the balloon, and
    - reducing the stent or scaffold outer diameter from the before crimping size to a first size,
    - wherein when the blades rotate about the aperture axis to reduce the stent or scaffold outer diameter, the balloon catheter rotates using a means for rotating.

20. The method of claim 19, wherein the means for rotating is at least one of a bearing supporting the catheter and a motor coupled to a channel that supports the catheter.

21. The method of claim 19, wherein the method is performed while a heating element warms the stent or scaffold.

* * * * *